United States Patent
Wilson et al.

(10) Patent No.: US 10,450,336 B2
(45) Date of Patent: Oct. 22, 2019

(54) NITROGEN-RICH MACROCYCLIC LIGANDS, CHELATION COMPLEXES THEREOF, AND PROCESS FOR SELECTIVE CHELATION OF RADIOACTIVE BISMUTH IONS WITH THE LIGANDS

(71) Applicant: Los Alamos National Security, LLC, Los Alamos, NM (US)

(72) Inventors: Justin Wilson, Los Alamos, NM (US); Eva Birnbaum, Los Alamos, NM (US); Kevin John, Santa Fe, NM (US); Francois Nortier, Los Alamos, NM (US); Michael Fassbender, Los Alamos, NM (US); Valery Radchenko, Los Alamos, NM (US); Jonathan Ward Engle, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 258 days.

(21) Appl. No.: 14/703,253

(22) Filed: May 4, 2015

(65) Prior Publication Data
US 2015/0344508 A1 Dec. 3, 2015

Related U.S. Application Data

(60) Provisional application No. 62/007,189, filed on Jun. 3, 2014.

(51) Int. Cl.
| | |
|---|---|
| *A61K 51/00* | (2006.01) |
| *A61M 36/14* | (2006.01) |
| *C07F 9/94* | (2006.01) |
| *C07D 401/14* | (2006.01) |
| *C07F 7/24* | (2006.01) |

(52) U.S. Cl.
CPC .............. *C07F 9/94* (2013.01); *C07D 401/14* (2013.01); *C07F 7/24* (2013.01)

(58) Field of Classification Search
CPC ............. C07F 9/94; C07F 7/24; C07D 401/14

USPC ....................................................... 424/1.11
See application file for complete search history.

(56) References Cited

U.S. PATENT DOCUMENTS 6,603,127 B1 * 8/2003 Scheinberg et al. ... 250/432 PD

FOREIGN PATENT DOCUMENTS

WO        WO 9501346 A1 *   1/1995

OTHER PUBLICATIONS

Di Vaira et al. J. Chem. Soc. Dalton Trans. 1992, 1127-1130.*
Di Vaira et al. J. Chem. Soc., Chem Commun. 1989, 126-127.*
Mandal et al. Inorg. Chem. 1997, 36, 5424-5425.*
Morfin et al. Inorg. Chimica Acta 2009, 362, 1781-1786.*
Chappell et al. Nucl. Med. Biol. 2000, 27, 93-100.*
Wang et al. Dalton Trans., 2003, 2379-2380.*
Jakubowski et al. J. Anat. At. Spectrom. 2008, 23, 1497-1507.*
Morgenstern et al. Curr. Radiopharm. 2012, 5, 221-227.*
Deal et al. J. Med. Chem. 1999, 42, 2988-2992.*
Zevaco et al. New J. Chem. 1991, 15, 927-930.*
Halime et al. Biochimie, 2009, 1318-1320.*
Yang et al. Synth. Reac. Inorg., Metal-Org. Nano-Met. Chem. 2013, 395-399.*

* cited by examiner

*Primary Examiner* — Michael G. Hartley
*Assistant Examiner* — Sean R Donohue
(74) *Attorney, Agent, or Firm* — Klarquist Sparkman, LLP

(57) ABSTRACT

Selective chelation of bismuth radionuclide ions from a mixture including actinium radionuclide ions involves exposing a ligand to an aqueous solution that includes bismuth radionuclide ions and actinium radionuclide ions under conditions whereby the bismuth radionuclide ions selectively chelate to the ligand for form cationic complexes of the bismuth radionuclide ions. and separating the cationic complexes of the bismuth radionuclide ions from the actinium radionuclide ions. The ligands have a structure based on a 12-membered cyclen ring and may include pendant functional groups that can be derivatized with biological targeting vectors for targeted alpha therapy.

7 Claims, 6 Drawing Sheets

NITROGEN-RICH MACROCYCLIC LIGANDS, CHELATION COMPLEXES THEREOF, AND PROCESS FOR SELECTIVE CHELATION OF RADIOACTIVE BISMUTH IONS WITH THE LIGANDS

BENEFIT CLAIM TO A RELATED APPLICATION

This application claims the benefit of U.S. Provisional Application No. 62/007,189 entitled "Nitrogen-Rich Macrocyclic Ligands, Chelation Complexes Therefor, and Process for Selective Chelation of Radioactive Bismuth Ions with Ligands," filed Jun. 3, 2014, incorporated by reference herein.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to macrocyclic ligands, to metal complexes with the ligands, and to selective chelation of bismuth radionuclides to form complexes that may be useful for targeted alpha therapy ("TAT").

BACKGROUND OF THE INVENTION

Targeted alpha therapy ("TAT") appears promising for treating tumors and other cancers. Targeted alpha therapy employs alpha-emitting radionuclides in combination with a biological targeting vector (e.g. tumor-targeting antibodies or peptides) to selectively destroy cancer cells. Proposed radionuclides for TAT include actinium-225 ($t_{1/2}$=9.9 days) and its shorter-lived daughter, bismuth-213 ($t_{1/2}$=45.6 minutes). FIG. 1 provides a schematic block diagram showing the radioactive decay of actinium-225 to bismuth-213. The actinium-225 may be obtained from a radioactive thorium source.

Actinium-225 and bismuth-213 (and also bismuth-212) have undergone clinical trials for cancer treatment with promising results.

Bismuth-212 and bismuth-213 may be used for TAT for the selective destruction of cancerous micro-metastases if an appropriate ligand and biological targeting vector (e.g. antibody, peptide) are employed to deliver these radionuclides to the cancerous cells and stabilize their location at the cancerous cells. The short penetration depth range of alpha particles in biological tissue would minimize toxic side effects resulting from damage of nearby healthy cells.

The rational design of ligands suitable for the chelation and delivery of bismuth ions to a desired location in vivo is difficult. The aqueous coordination chemistry of bismuth ion has been scarcely explored and therefore it is poorly understood. While a variety of ligands have been synthesized and tested for chelation of bismuth radioisotopes, no ideal ligand has been found. In practice, the complexes of bismuth were unstable in vivo; they decomposed, and the resulting uncomplexed bismuth ions distributed to the kidneys.

Ligands that can be functionalized with a biological targeting vector and reacted with a suitable radionuclide to form a complex that is stable in vivo are desirable for targeted alpha therapy.

SUMMARY OF THE INVENTION

An embodiment relates to a process for preparing a complex of a bismuth radionuclide. The process includes exposing a ligand to an aqueous solution that includes bismuth radionuclide ions and actinium radionuclide ions under conditions where the bismuth radionuclide ions selectively chelate to the ligand to form cationic complexes of the bismuth radionuclide ions. The process also includes separating the cationic complexes of the bismuth radionuclide ions from uncomplexed actinium radionuclide ions.

Another embodiment relates to compounds that have a structural formula

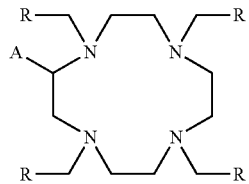

wherein A is selected from hydrogen and

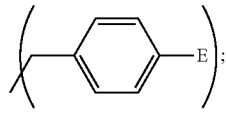

wherein E is selected from —NO$_2$, —NH$_2$, —SCN, —N$_3$, -alkyne (terminal), alkyne (strained), maleimide, iodoacetamide, —NH(—C=S)NH—Z, triazole-Z, thioether-Z; wherein Z is a peptide, antibody, antibody fragment, peptide nucleic acid, nanoparticle, or other targeting moiety; wherein R is selected from

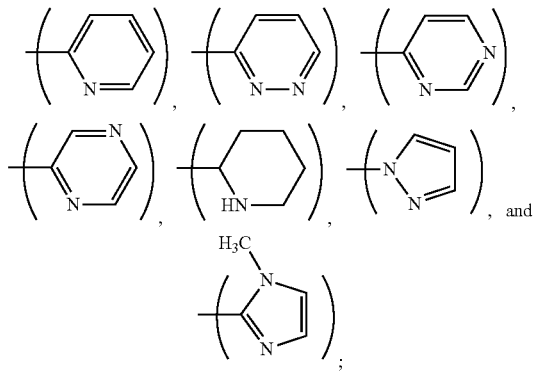

with the caveat that R is not

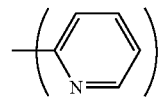

when A is hydrogen.

Another embodiment relates to a cationic chelation complex having the structural formula

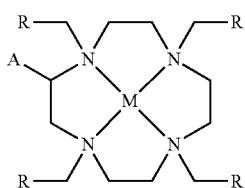

wherein M is a metal ion;
wherein A is selected from hydrogen and

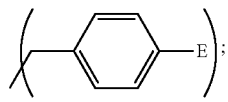

wherein E is selected from —NO$_2$, —NH$_2$, —SCN, —N$_3$, -alkyne (terminal), alkyne (strained), maleimide, iodoacetamide, —NH(—C=S)NH—Z, triazole-Z, thioether-Z;
wherein Z is a peptide, antibody, antibody fragment, peptide nucleic acid, nanoparticle, or other targeting moiety;
wherein R is selected from

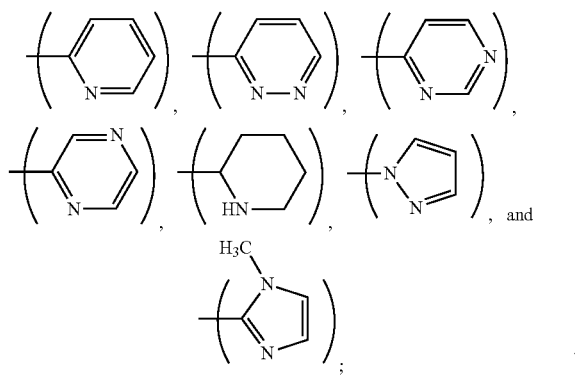

with the caveat that R is not

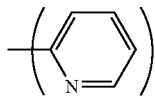

when A is hydrogen.

DETAILED DESCRIPTION

Figure 1:
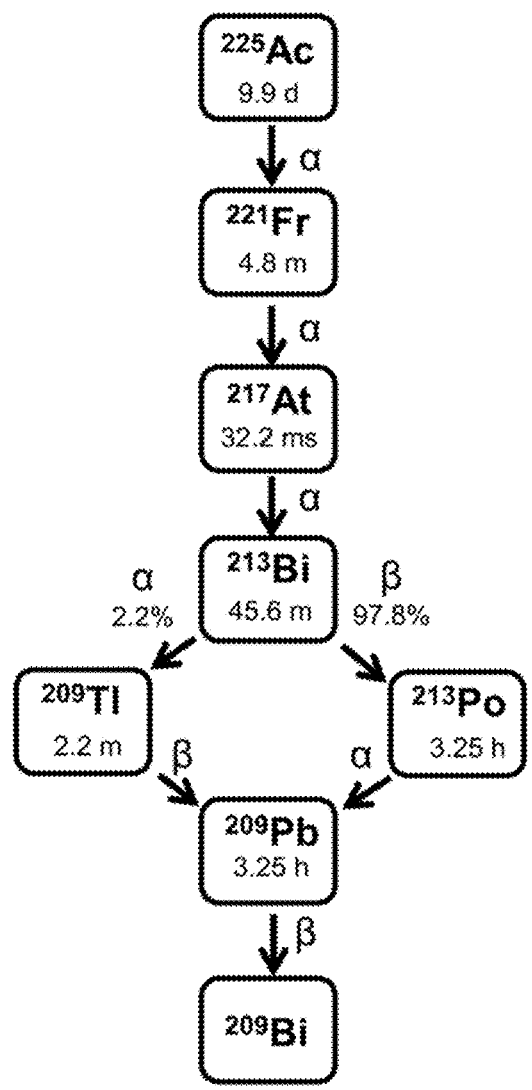
FIG. 1 shows a schematic block diagram of the radioactive decay chain of actinium-225 to bismuth-213.

An aspect of this invention relates to nitrogen-rich macrocyclic compounds. Another aspect relates to chelation of metal ions with these macrocyclic compounds. Another aspect relates to the selective chelation of bismuth radionuclide ions in the presence of competing quantities of other radionuclide ions. Yet another aspect relates to chelation of these nitrogen-rich macrocyclic ligands with lanthanide(III) ions.

Structural formulas of some embodiment nitrogen-rich macrocyclic compounds include those identified below as L$^{pyd}$, L$^{pyr}$, and L$^{pz}$.

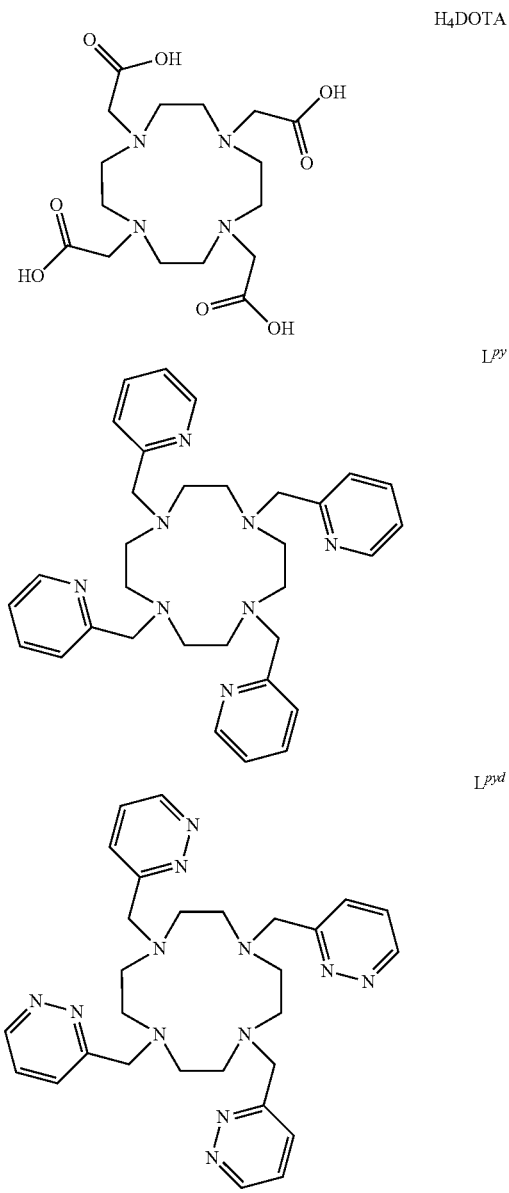

L^{pyr}

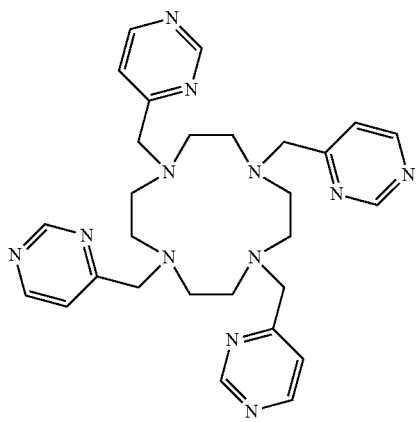

L^{pz}

Also shown above are structural formulas for the known ligands referred to as $L^{py}$ and $H_4$DOTA. These compounds are also referred to herein as ligands or chelation ligands because they may be used to form complexes (chelation complexes in particular) with metal ions such as but not limited to, bismuth ions and lanthanide ions.

The ligands $L^{py}$, $L^{pyd}$, $L^{pyr}$, and $L^{pz}$ were prepared. These ligands were synthesized and their complexation chemistry with bismuth radionuclide ions in the presence of competing quantities of other radionuclide ions was investigated.

In an experiment, $L^{py}$ was reacted with an aqueous solution of radionuclide ions; the aqueous solution included actinium-225 ions and bismuth-213 ions. The result was selective chelation of $L^{py}$ to the bismuth-213 ions. The ligands $L^{pyd}$, $L^{pyr}$, and $L^{pz}$ also selectively complex to bismuth, or are expected to selectively complex to bismuth, in the presence of competing quantities of other radionuclide ions.

The chelation complexes resulting from reacting these ligands with bismuth radionuclide ions (e.g. bismuth-213, bismuth-212, bismuth-207, etc.) are kinetically and thermodynamically stable in vivo, or are expected to be kinetically and thermodynamically stable complexes in vivo.

Embodiment ligands $L^{pyd}$, $L^{pyr}$, and $L^{pz}$ (as well as $L^{py}$) are based on 1,4,7,10-tetraazacyclododecane-1,4,7,10-tetraacetic acid ("$H_4$DOTA"). $H_4$DOTA contains a macrocyclic cyclen base with four pendant carboxylic acid groups. The carboxylic acid groups may dissociate protons to form carboxylate groups. Anionic, octadentate lanthanide complexes of DOTA are stable in aqueous solutions. $L^{py}$ may be considered an analogue of $H_4$DOTA in which the pendant carboxylic acid groups are replaced with pyridines.

Scheme 1 below summarizes the syntheses of $L^{py}$, $L^{pyd}$, $L^{pyr}$, and $L^{pz}$ by reacting cyclen (i.e. 1,4,7,10-tetraazacyclodecane) with various heterocyclic compounds.

Scheme 1.

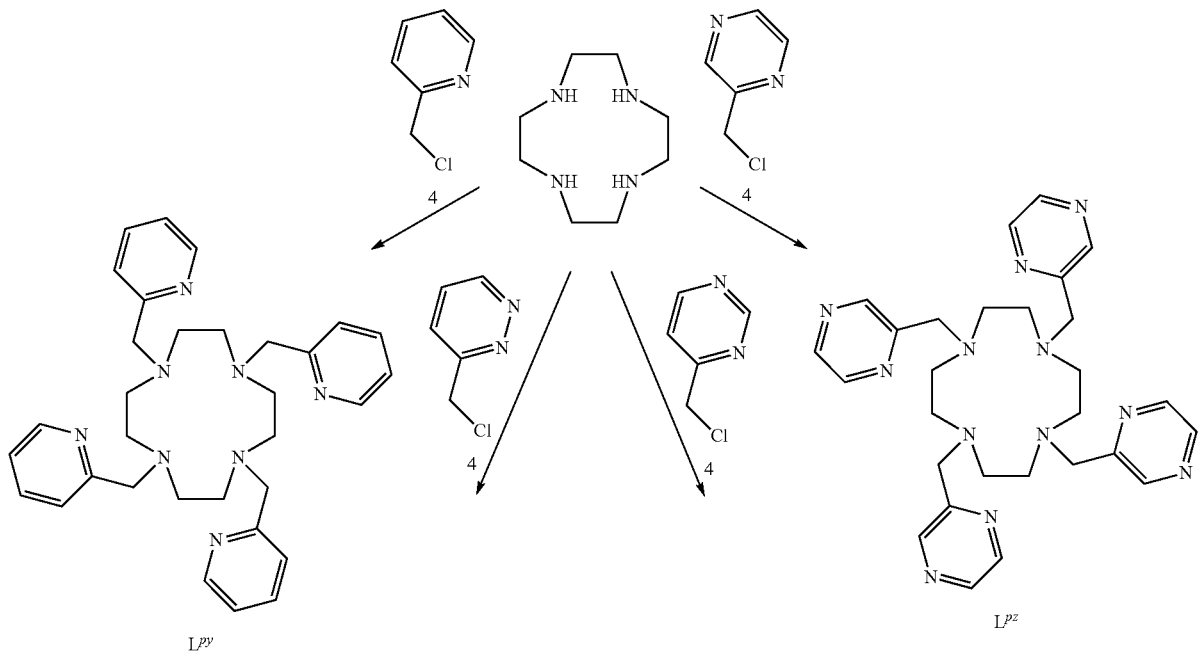

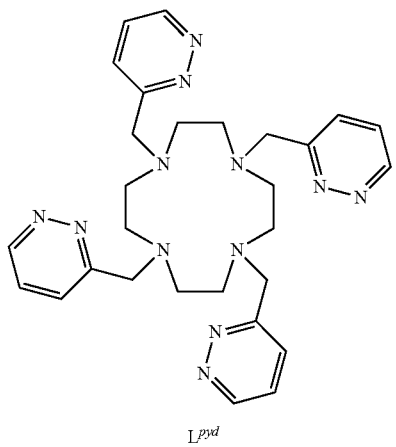

$L^{pyd}$

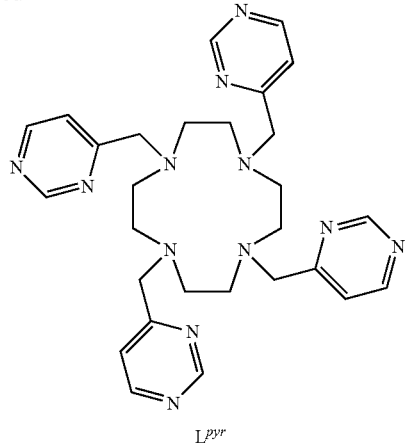

$L^{pyr}$ $L^{py}$ (Scheme 1, far left) was synthesized by a known procedure involving reaction of slightly greater than four equivalents of 2-picolylchloride with cyclen in the presence of excess $Cs_2CO_3$ (20 equivalents) in refluxing $CH_3CN$. $L^{pyd}$, $L^{pyr}$, and $L^{pz}$, were synthesized in moderate yields using the corresponding chloromethyl N-heterocycles shown in Scheme 1. The chloromethyl N-heterocycles were synthesized by reacting the corresponding methyl N-heterocycles with ⅓ equiv of trichloroisocyanuric acid in refluxing chloroform (see: Schiess et al., *Org. Lett.* 2011, 13, 1436, incorporated by reference). The chloromethyl N-heterocycles were purified by column chromatography prior to reactions with cyclen.

The ligands $L^{py}$, $L^{pyr}$, $L^{pyd}$, and $L^{pz}$ were characterized by elemental analysis (EA), APCI-MS, IR, $^1H$, and $^{13}C$ NMR spectroscopy. EA and APCI-MS were consistent with the proposed molecular formulas. $^1H$ and $^{13}C$ NMR spectroscopy indicated a high degree of symmetry in solution, likely arising from conformational non-rigidity. All of the hydrogen atoms on the cyclen backbone were magnetically equivalent, and produced a singlet in the $^1H$ NMR spectrum at 2.75 ppm. For each of the four ligands, the protons on the methylene bridge connecting the N-heterocycles with cyclen were also magnetically equivalent and gave rise to a broad singlet between 3.65 and 3.78 ppm.

Figure 4:
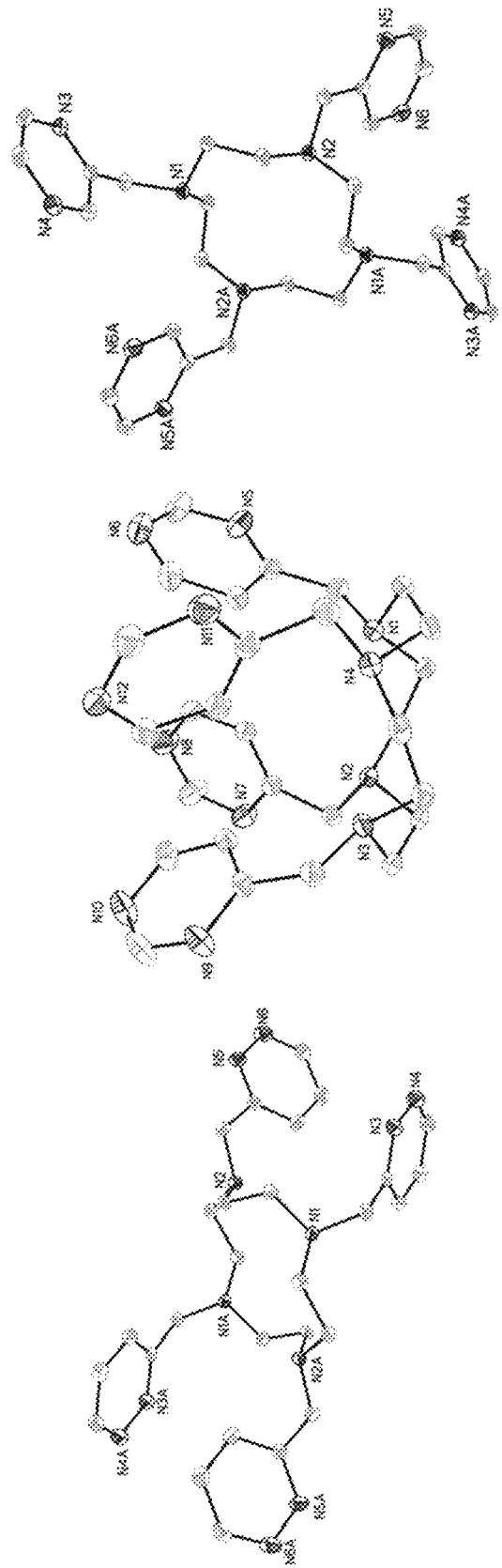
FIG. 4 shows X-ray crystal structures of L$^{pyd}$ (left), L$^{pyr}$ (center), and L$^{pz}$ (right). Hydrogen atoms were omitted for clarity. Ellipsoids are drawn at 50% probability levels.

The ligands were also characterized by single-crystal X-ray diffraction. Their crystal structures are shown in FIG. 4. Despite the similar chemical structures, the unit cell parameters of the ligands were different. $L^{pyd}$ and $L^{pz}$ were centrosymmetric and included inversion centers in the middle of the cyclen macrocycle. $L^{pyr}$ crystallized in a puckered conformation in which the four pyrimidine heterocycles sat on the same face of the cyclen.

Details relating to materials used for synthesizing embodiment ligands and instruments used for making various physical measurements now follow. Solvents used were of analytical grade. $Cs_2CO_3$ was purchased from Acrōs Organics. Cyclen and $La(OTf)_2$ were purchased from Strem Chemicals. The ligand $L^{py}$ was synthesized as previously reported. The chloromethyl N-heterocycles were synthesized by the reaction of trichloroisocyanuric acid and the methyl N-heterocycle, and were purified by $SiO_2$ gel column chromatography, eluting with either 100% ethyl acetate or 100% diethyl ether (stabilized with 1-2% ethanol), as described in the literature. The residual solvent content in these products, which are viscous oils, was quantified by NMR spectroscopy and incorporated in the molecular weight used for calculating proper stoichiometric quantities. Reactions were carried out under normal atmospheric conditions with no efforts to exclude atmospheric moisture or oxygen.

FTIR spectra were acquired with a Thermo Scientific Nicolet iS10 in the attenuated total reflectance (ATR) mode with a diamond ATR crystal accessory. Relative peak intensities are reported as very strong (vs), strong (s), medium (m), weak (w), or very weak (vw). Elemental analyses of carbon, nitrogen, and hydrogen, were performed by ALS Environmental, Tucson, Ariz., USA. NMR spectra were acquired with a BRUKER Avance III HD 400 MHz spectrometer interfaced with TopSpin v3.2 software. In deuterated organic solvents, chemical shifts were referenced internally to residual protic solvent peaks. For NMR spectra acquired in $D_2O$, shifts were referenced internally to either residual acetonitrile or to a small amount of added 1,4-dioxane. For variable-temperature experiments, the temperatures were corrected using an ethylene glycol chemical shift thermometer. Correction factors were generally less than 1 K. Samples of 1-4 (vide supra) were prepared in $D_2O$ at concentrations of 25 to 50 mM. The pD values of the solutions were not adjusted, but were found to be consistently between 6.5 to 7.0 with pH paper. Line-shape analysis of the two coalescing $^{13}C$ resonances was carried out using the DNMR module of Bruker's TopSpin v3.2 software. Variable-temperature runs were carried out two times with independently prepared samples. The combined data of the two runs were combined on a single Eyring plot. Errors quoted are derived from the standard errors of the least squares fit to the linear equation. Eyring analyses of 3 and 4 were complicated by the observation of significant complex decomposition at temperatures greater than 45° C. Therefore line shape analysis was only carried out in the 5-45° C. range. Because this narrow temperature range precludes the analysis of rate constants near and above the coalescence temperature, a greater error was associated with the Eyring analyses of these two complexes.

Synthesis of 1,4,7,10-Tetrakis(3-pyridazylmethyl)-1,4,7,10-tetraazacyclododecane, (i.e. $L^{pyd}$)

To a mixture of 233 mg (1.35 mmol) cyclen and 8.8 g (27 mmol) of $Cs_2CO_3$ in 6 mL of $CH_3CN$ was added a solution of 3-(chloromethyl)pyridazine.3.6EtOH (1.67 g, 6.57 mmol) in 9 milliliters ("mL") of $CH_3CN$ in a dropwise manner. The resulting suspension was then heated to reflux for 16 hours ("h"). The dark orange-brown mixture was filtered through a pad of Celite while still hot. The solid residue that remained on the Celite pad was washed with 5×5 mL boiling $CH_3CN$ until the eluate was colorless. The combined filtrate and washings were evaporated to dryness under reduced pressure at 40° C., leaving a brown residue. The residue was taken up in 3 mL of $CH_3CN$. The red-brown supernatant was carefully separated from the beige solid with a Pasteur pipette, and the solid was washed an additional three times with 3 mL $CH_3CN$. The solid was then dissolved in 10 mL boiling $CH_3CN$, and the resulting orange solution was filtered through a column of Celite while still hot to remove some solid impurities. The filtrate was stored at −20° C. for 5 h, giving rise to pale orange crystals of the desired compound. The supernatant was decanted from the crystals, which were washed sequentially with 3×5 mL cold (−20° C.) $CH_3CN$ and 3×5 mL $Et_2O$ and then dried in air. Yield: 315 mg, 43%. $^1$H NMR (400 MHz, $CDCl_3$): δ=9.04 (4H, d), 7.65 (4H, d), 7.35 (4H, dd), 3.78 (8H, s), 2.75 (16H, s). $^{13}C\{^1H\}$ NMR (100 MHz, $CDCl_3$): δ=161.9, 150.5, 127.0, 126.6, 59.6, 53.3. IR (ATR, cm$^{-1}$): 2938 w, 2824 m, 2785 m, 5179 m, 1555 w, 1453 s, 1431 s, 1399 s, 1371 s, 1355 s, 1307 s, 1288 s, 1265 s, 1250 s, 1185 m, 1152 m, 1133 s, 1094 s, 1079 s, 1068 s, 1046 s, 1008 s, 996 s, 961 m, 923 s, 844 w, 823 s, 780 s, 749 s. APCI-MS (positive ion mode, MeOH): 541.5 (calcd. for [M+H]$^+$ 541.3). Anal. calcd. for $L^{pyd}$, $C_{28}H_{36}N_{12}$: C, 62.20; H, 6.71; N, 31.09. Found: C, 62.34; H, 6.75; N, 30.96.

Synthesis of 1,4,7,10-Tetrakis(4-pyrimidylmethyl)-1,4,7,10-tetraazacyclododecane, (i.e. $L^{pyr}$)

To a mixture of 517 mg (3.00 mmol) cyclen and 20.5 g (62.9 mmol) of $Cs_2CO_3$ in 15 mL of $CH_3CN$ was added a solution of 4-(chloromethyl)pyrimidine.0.75EtOAc (2.45 g, 12.6 mmol) in 10 mL of $CH_3CN$ in a dropwise manner. The resulting suspension was then heated to reflux for 16 h. The dark red-orange mixture was filtered through a pad of Celite while still hot. The pale brown solid residue that remained on the Celite pad was washed with 5×5 mL boiling $CH_3CN$ until the eluate was colorless. The combined filtrate and washings were evaporated to dryness under reduced pressure at 40° C., leaving a red oily residue. The residue was taken up in 5 mL of $CH_3CN$ and cooled in an ice bath for 15 minutes ("min"). A pale-orange solid was separated from the dark red solution by decanting. The remaining solid was washed with 2×5 mL $CH_3CN$ and then dissolved in 16 mL boiling $CH_3CN$. The orange-red solution was filtered through a column of Celite while still hot and then stored at −20° C. for 16 h. Pale orange crystalline solid deposited, which was separated from the orange supernatant by decanting. The solid was washed sequentially with 3×2 mL cold (−20° C.) $CH_3CN$ and 3×2 mL $Et_2O$ and then dried in air. Yield: 594 mg, 37%. $^1$H NMR (400 MHz, $CDCl_3$): δ=9.08 (4H, s), 8.51 (4H, d), 7.69 (4H, d), 3.62 (8H, s), 2.78 (16H, s). $^{13}C\{^1H\}$ NMR (100 MHz, $CDCl_3$): δ=168.8, 158.7, 157.1, 120.1, 60.9, 53.8. IR (ATR, cm$^{-1}$): 2794 m, 1578 vs, 1548 s, 1471 m, 1436 m, 1384 s, 1360 s, 1307 m, 1293 s, 1248 m, 1158 w, 1108 s, 1071 w, 994 m, 973 m, 902 s, 869 s. 834 s, 798 s, 777 s, 739 s, 677 m. APCI-MS (positive ion mode, MeOH): 541.2 (calcd. for [M+H]$^+$ 541.3). Anal. calcd. for $L^{pyr}$, $C_{28}H_{36}N_{12}$: C, 62.20; H, 6.71; N, 31.09. Found: C, 61.88; H, 6.78; N, 30.75.

Synthesis of 1,4,7,10-Tetrakis(2-pyrazinylmethyl)-1,4,7,10-tetraazacyclododecane, (i.e. $L^{pz}$)

To a mixture of 333 mg (1.93 mmol) cyclen and 13.0 g (39.9 mmol) of $Cs_2CO_3$ in 15 mL of $CH_3CN$ was added a solution of 2-(chloromethyl)pyrazine.0.13EtOH (1.14 g, 8.48 mmol) in 10 mL of $CH_3CN$ in a dropwise manner. The resulting suspension was then heated to reflux for 16 h. The yellow-brown mixture was filtered through a pad of Celite while still hot. The pale brown solid residue that remained on the Celite pad was washed with 3×5 mL boiling $CH_3CN$. The combined orange filtrate and washings were stored at 20° C. for 4 h. The mix was then filtered to collect the product as an off-white crystalline solid. The solid was washed sequentially with 3×5 mL cold (−20° C.) $CH_3CN$ and 3×5 mL $Et_2O$ and then dried in air. Yield: 639 mg, 61%. $^1$H NMR (400 MHz, $CDCl_3$): δ=8.78 (4H, s), 8.43 (8H, d+d), 3.65 (8H, s); 2.76 (16H, s). $^{13}C\{^1H\}$ NMR (100 MHz, $CDCl_3$): δ=155.3, 145.7, 143.8, 143.2, 59.6, 53.6. IR (ATR, cm$^{-1}$): 2947 w, 2802 m, 1479 w, 1455 m, 1430 m, 1397 s, 1369 s, 1353 s, 1308 vs, 1295 m, 1233 w, 1154 m, 1134 s, 1081 vs, 1064 m, 1049 m, 1013 s, 924 s, 859 s, 830 s, 803 m, 749 w, 660 w. APCI-MS (pos ion mode, MeOH): 541.2 (calcd. for [M+H]$^+$ 541.3). Anal. calcd. for $L^{pz}$, $C_{28}H_{36}N_{12}$: C, 62.20; H, 6.71; N, 31.09. Found: C, 62.24; H, 6.78; N, 30.88.

Figure 2:
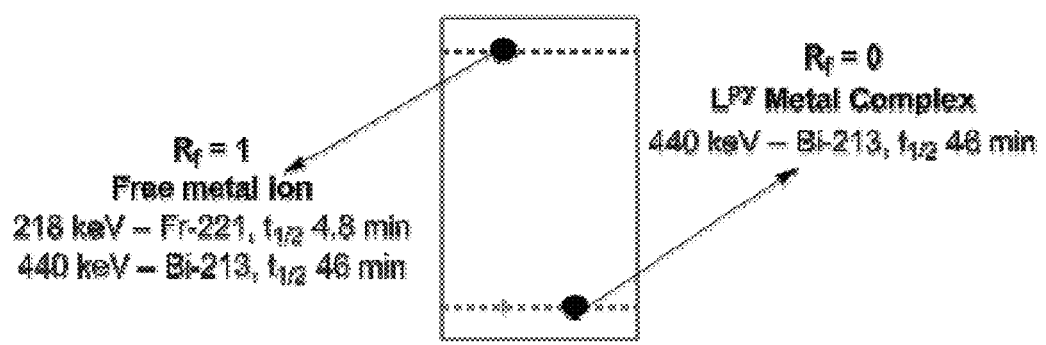
FIG. 2 shows radio-TLC results of labeling an equilibrium mixture of Ac-225 and its daughters with ligand L$^{py}$.

An aspect of this invention relates to selective complexation (i.e. radiolabeling) of ligands with bismuth radionuclide ions. With the aforementioned ligands in hand, the competitive radiolabeling of $L^{py}$ with a mixture of radionuclides including both Ac-225 and Bi-213 was examined. First, Ac-225 was eluted from a thorium-229 (i.e. Th-229) cow. The solution of Ac-225 was allowed to equilibrate, which provided a mixture of radionuclides including Ac-225 and its daughter isotopes, among which is Bi-213. The solvent from the solution was evaporated, and the residue was dissolved in an aqueous solution of 1 M ammonium acetate ($NH_4OAc$) at pH 5 for the radiolabeling. $L^{py}$ was added. The concentration of $L^{py}$ was 2 mM. The reaction mixture was analyzed by radio-thin-layer-chromatography ("radio-TLC") after 30 minutes using a plate containing a solid-phase $SiO_2$ and a mobile phase of an aqueous solution of 0.4 M sodium citrate at pH 4. The uncomplexed metal ions migrated with the solvent front ($R_f$=1) while metal-complexes of $L^{py}$ remained at the baseline ($R_f$=0) (see FIG. 2).

The plate was cut in half into a top fraction and a bottom fraction; each half was analyzed by gamma spectroscopy. The gamma spectrum for the top half (i.e. Rf=1) included strong gamma lines at 218 keV and 440 keV which corresponded to uncomplexed metal ions of Fr-221 and Bi-213, respectively, which are both daughter isotopes of Ac-225. The gamma spectrum for the bottom half of the TLC plate included an emission line at 440 keV due to Bi-213; no emission from Fr-221 was detected in the bottom half.

Gamma spectra for the top half and bottom half were obtained again after 24 hours. The gamma spectrum for the top half after 24 hours still included emission lines 218 keV and 440 keV with strong intensities. No gamma emissions were detected from the bottom half. These observations are consistent with the following explanation: the bottom half of the TLC plate contained only Bi-213, which decayed entirely over the 24 hour period due to its short half-life of 45 min. The top half of the TLC plate contained Ac-225. The strong emission lines at 218 keV and 440 keV present in the gamma spectrum of the top half may be explained by the radioactive decay of uncomplexed Ac-225 (see FIG. 1) present in the top half. The observation of gamma emissions after 24 hours is consistent with the presence of Ac-225 ($t_{1/2}$=9.9 days). Collectively, these results indicate that $L^{py}$ selectively chelates Bi-213 ions even in the presence of competing quantities of Ac-225 ions.

Figure 3:
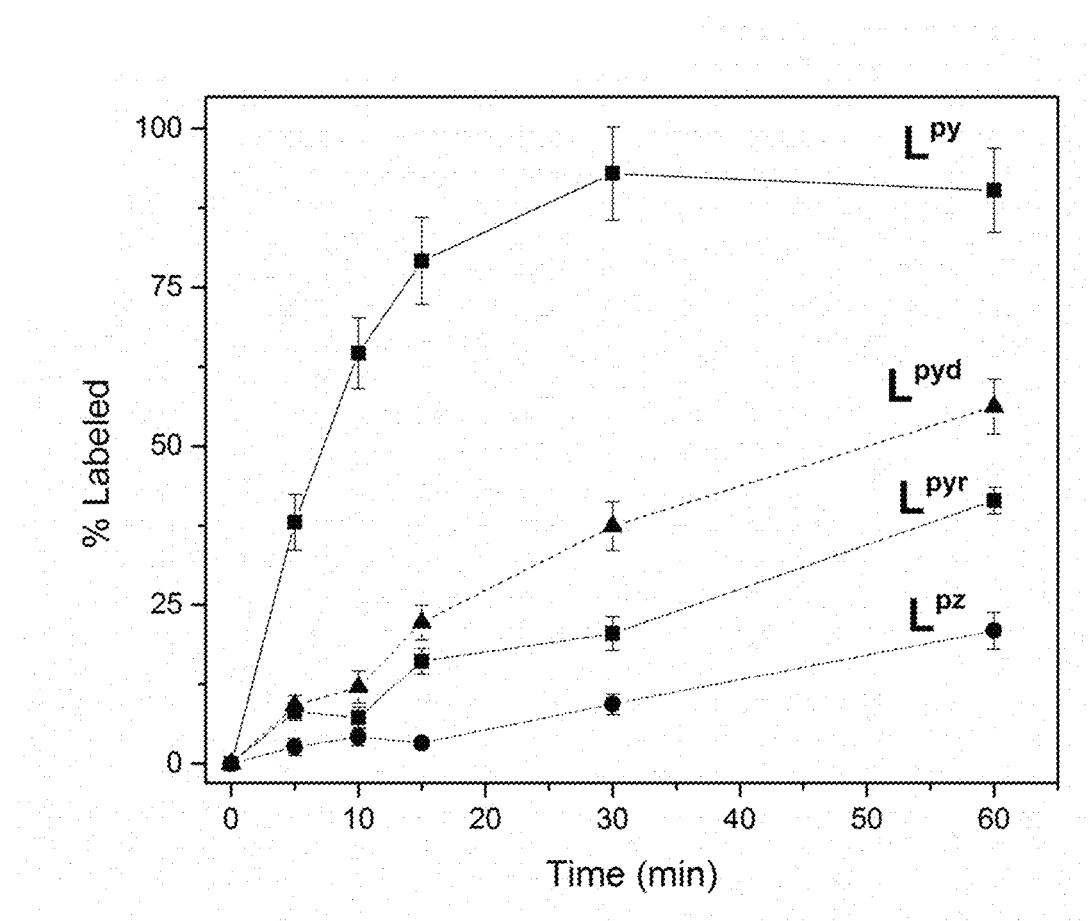
FIG. 3 shows a graph of kinetics data obtained from radiolabeling experiments of embodiment ligands with Bi-207.

The radiolabeling kinetics of the ligands $L^{py}$, $L^{pyd}$, $L^{pyr}$, and $L^{pz}$ with bismuth ions was examined using Bi-207 ($t_{1/2}$=32 years) because it has a much longer half life than Bi-213. Solutions having concentrations of 1, 10, 100, and 1000 micromolar ("μM") of each of the ligands were prepared. Each solution was combined with 3 kBq of Bi-207. The reaction temperature was ambient room temperature (21±2° C.). Aliquots of each reaction mixture were obtained during the reaction and analyzed by radio-TLC. The rates of reaction (i.e. the radiolabeling kinetics) between the bismuth ions and the ligands were dependent on the individual ligand and also on the concentration of the ligand. At a ligand concentration of 1 μM, a maximum of 50% labeling was observed after 60 minutes. At a ligand concentration of 1000 micromolar, the reaction was nearly 100% complete (i.e. 100% of the ligand was labeled with Bi-207) after 5 minutes. FIG. 3 provides a graph of the radiolabeling kinetics for the four ligands at a ligand concentration of 100 μM. According to FIG. 3, $L^{py}$ formed complexes the most rapidly, followed sequentially by $L^{pyd}$, $L^{pyr}$, and $L^{pz}$. By comparison, chelation of Bi-213 with the known ligands DOTA and CHX-DTPA requires heating to 90° C.

Bi-213 is a preferred therapeutic isotope for TAT. Because it has a short half-life, radiolabeling kinetics should be rapid. Embodiment ligands bind rapidly to bismuth ions, and thus these ligands appear to be particularly attractive for chelation of bismuth ions such as Bi-213. These ligands are nitrogen-rich macrocycles that are good candidates for the selective, stable, and rapid chelation of bismuth radioisotopes.

Embodiment complexes with bismuth ions are thermally and kinetically stable, or are expected to be thermally and kinetically stable in vivo. They are expected to be thermally and kinetically stable under the conditions present in biological serum and tissue so they can arrive at their target cancer cells and destroy these cells. Preliminary data indicate that the Bi$L^{py}$ complex is stable against 200 mM citrate and 40 mg/mL bovine serum albumin for 24 h. With these results and expectations related to the stability of complexes in vivo, analogs of these ligands may be prepared that can be derivatized further with vectors chosen for specific targets in host for targeted alpha therapy. Thus, embodiment ligands also include analogs of the ligands $L^{py}$, $L^{pyr}$, $L^{pyd}$, and $L^{pz}$ in which one or more of the pendant heterocycles includes a reactive functional group such as but not limited to a thiocyanate group, an amine group, an alkyne group, an azide group, and a carboxylic acid group. These ligands have the structural formula

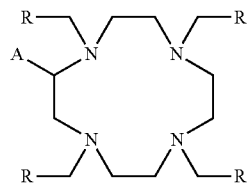

wherein A is

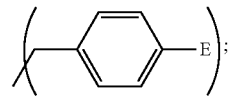

wherein E is selected from wherein E is selected from —NO$_2$, —NH$_2$, —SCN, —N$_3$, -alkyne (terminal), alkyne (strained), maleimide, iodoacetamide;

wherein R is selected from

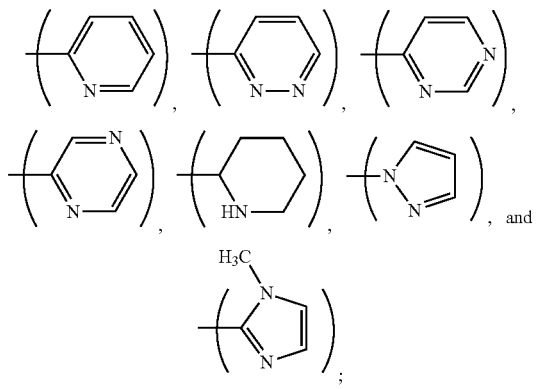

Scheme 2 below illustrates a synthesis of embodiment ligands that can be later be derivatized with a biological or targeting vector such as a peptide or an antibody.

Scheme 2.

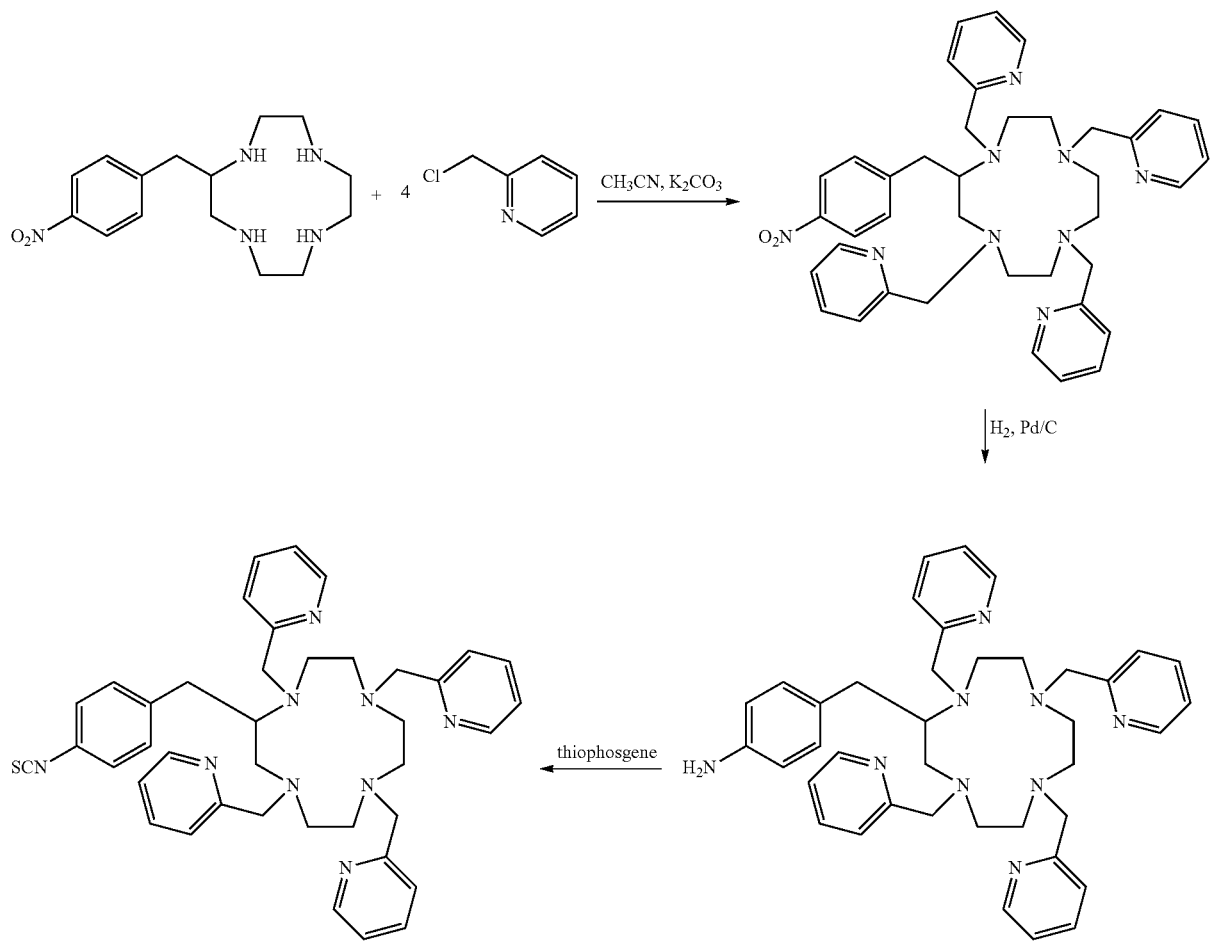

Embodiments in which reactive functional group E is —NH₂ or —SCN can be reacted with a chosen reactant including a biological targeting vector such as an antibody or a peptide. The biological targeting vector may be chosen to deliver the bismuth complex to a desired target where the alpha particles emitted from the radioactive complex can destroy the cancer cells. The —SCN functional group can be reacted with amino functional groups found in peptides and antibodies. The amino functional groups are present either at the N-terminus or as side-chains of lysine residues. This reaction forms a stable thiourea linkage between the chelator and the biological targeting vector. The —NH₂ functional group can be reacted with carboxylic acid functional groups of peptides and antibodies. These reactions required the used of another chemical reagent to activate the carboxylic acids. Such reagents include but are not limited to 1,1'-carbonyldiimidazole, 1-[bis(dimethylamino)methylene]-1H-1,2,3-triazolo[4,5-b]pyridinium 3-oxid hexafluorophosphate (HATU), 1-ethyl-3-(3-dimethylaminopropyl)carbodiimide (EDC), O-(benzotriazol-1-yl)-1,1,3,3-tetramethyluronium hexafluorophosphate (HBTU), and N,N'-dicyclohexylcarbodiimide (DCC). These reactions form stable amide bonds between the biological targeting vector and the chelating agent. After conjugations of the chelators to the targeting vector, the constructs can be labeled with Bi-213. Scheme 3 below illustrates bioconjugation reactions of this type. The sphere represents antibodies, peptides, antibody fragments, peptide nucleic acids, and nanoparticles.

Scheme 3.

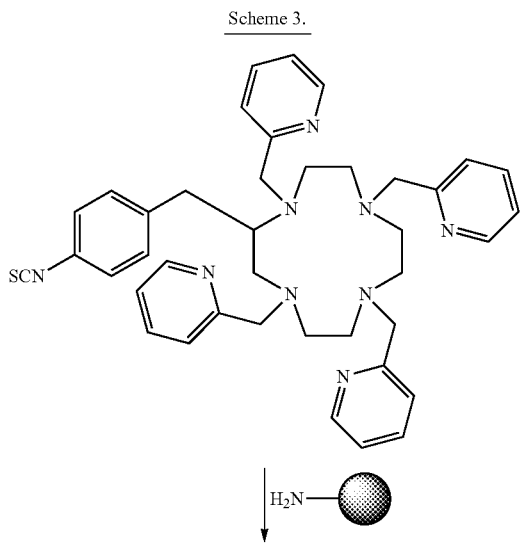

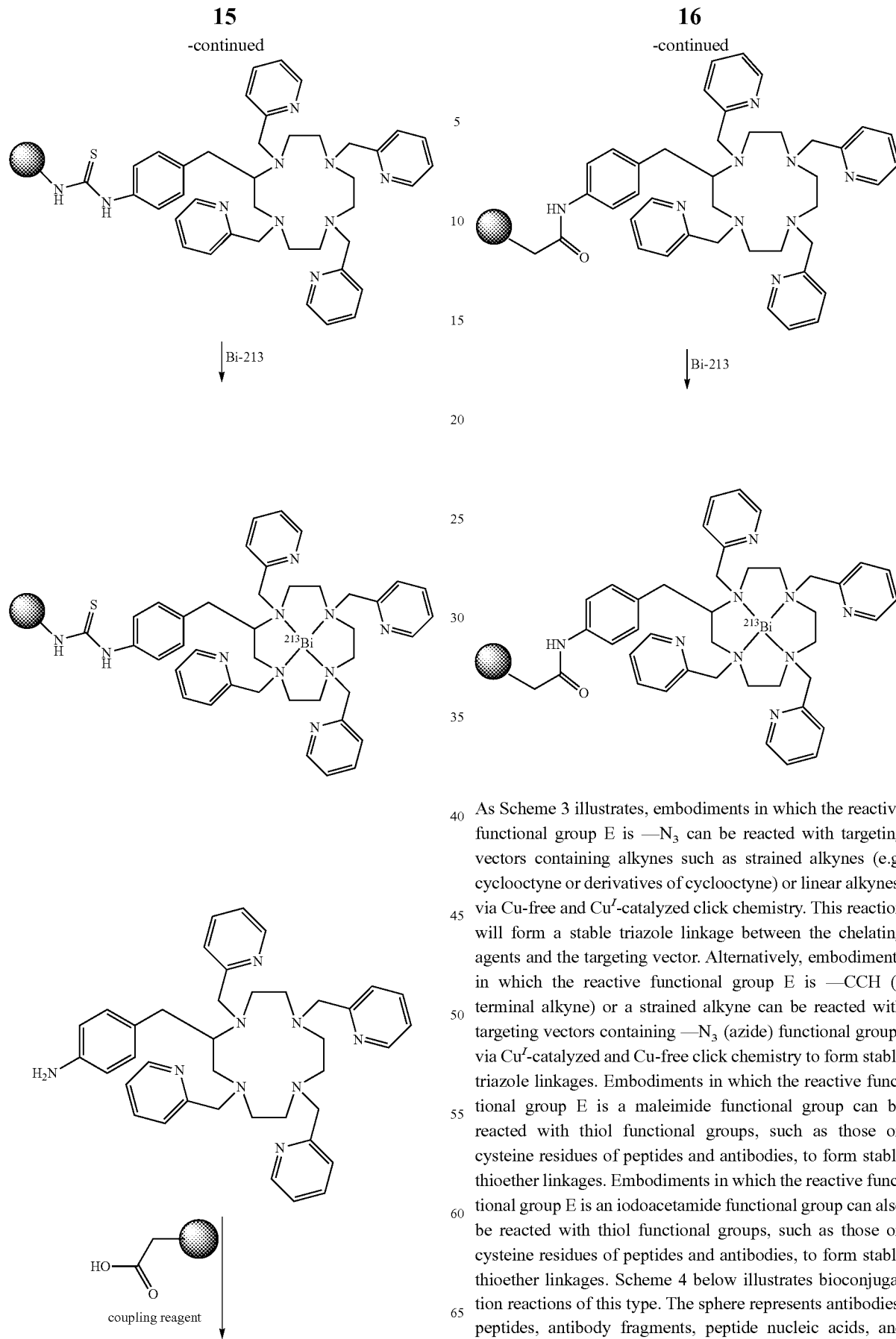

As Scheme 3 illustrates, embodiments in which the reactive functional group E is —N₃ can be reacted with targeting vectors containing alkynes such as strained alkynes (e.g. cyclooctyne or derivatives of cyclooctyne) or linear alkynes, via Cu-free and Cu$^I$-catalyzed click chemistry. This reaction will form a stable triazole linkage between the chelating agents and the targeting vector. Alternatively, embodiments in which the reactive functional group E is —CCH (a terminal alkyne) or a strained alkyne can be reacted with targeting vectors containing —N₃ (azide) functional groups via Cu$^I$-catalyzed and Cu-free click chemistry to form stable triazole linkages. Embodiments in which the reactive functional group E is a maleimide functional group can be reacted with thiol functional groups, such as those on cysteine residues of peptides and antibodies, to form stable thioether linkages. Embodiments in which the reactive functional group E is an iodoacetamide functional group can also be reacted with thiol functional groups, such as those on cysteine residues of peptides and antibodies, to form stable thioether linkages. Scheme 4 below illustrates bioconjugation reactions of this type. The sphere represents antibodies, peptides, antibody fragments, peptide nucleic acids, and nanoparticles.

Scheme 4.
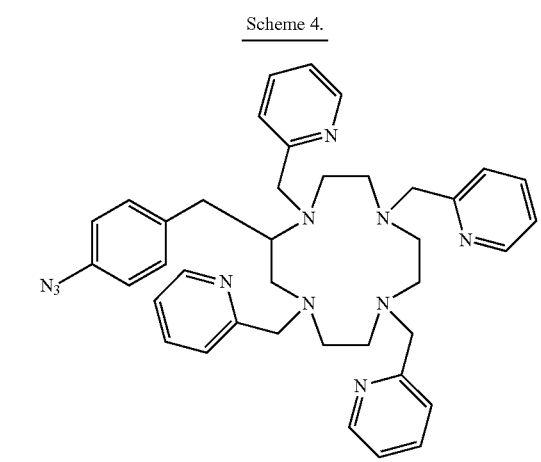
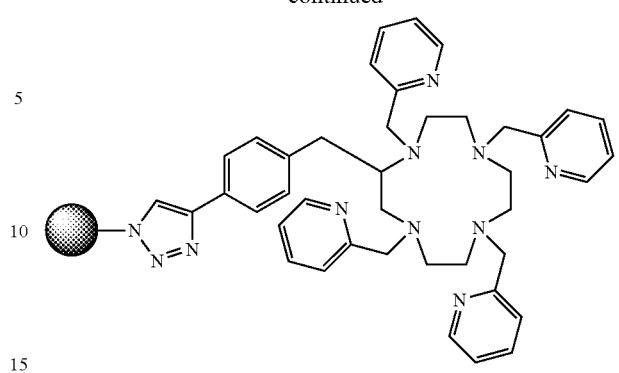
Cu-free or Cu-catalyzed
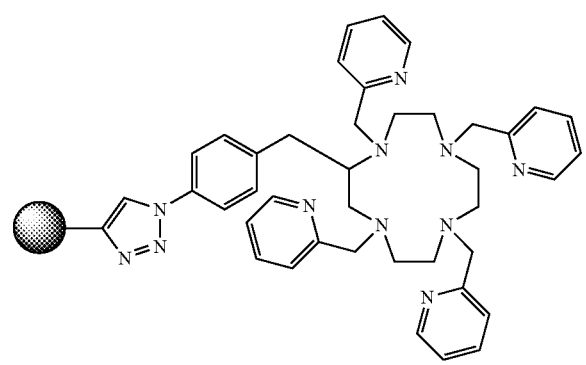
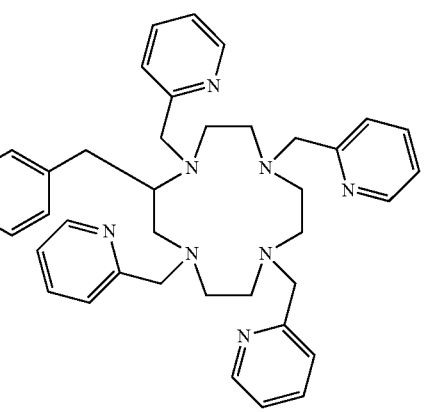
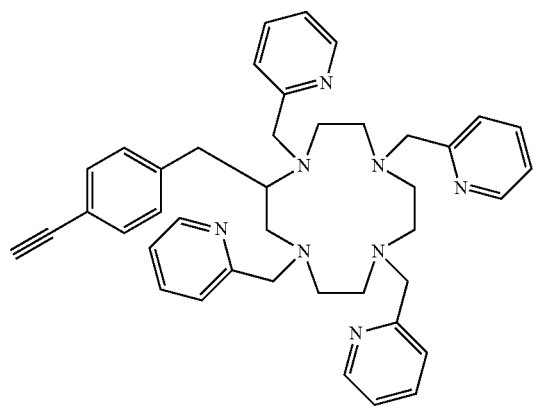
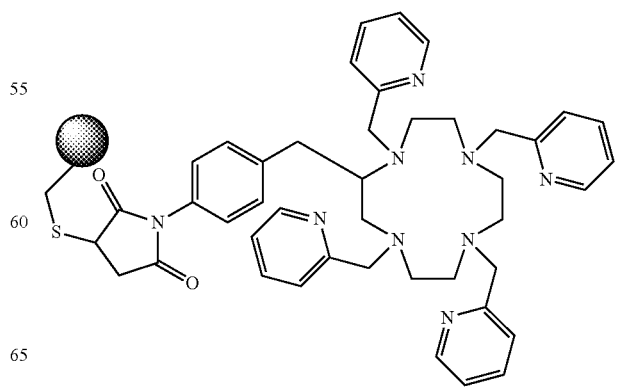

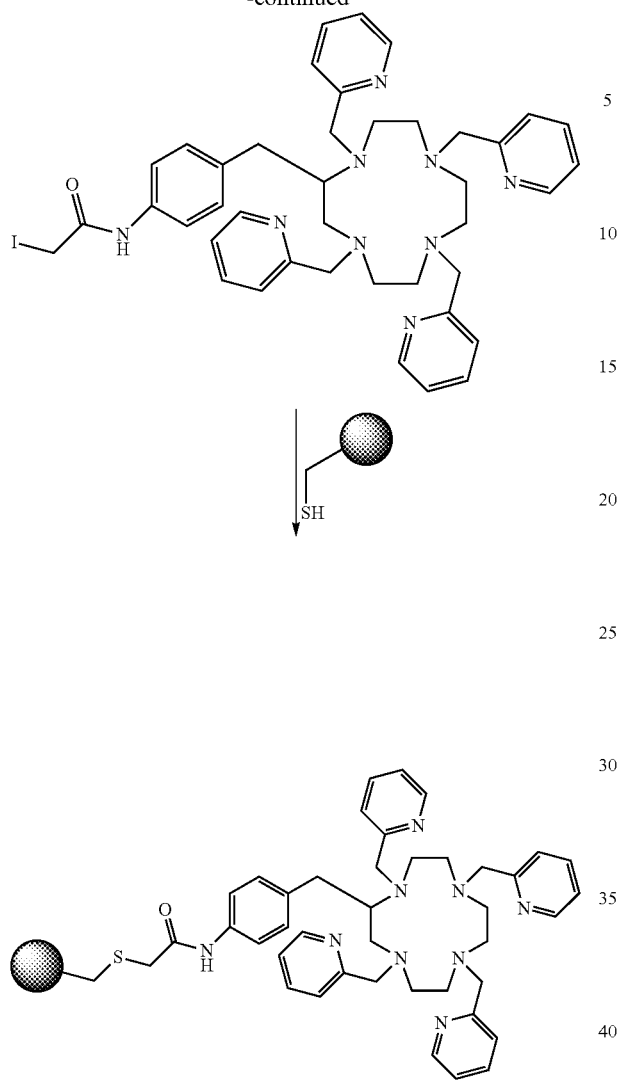

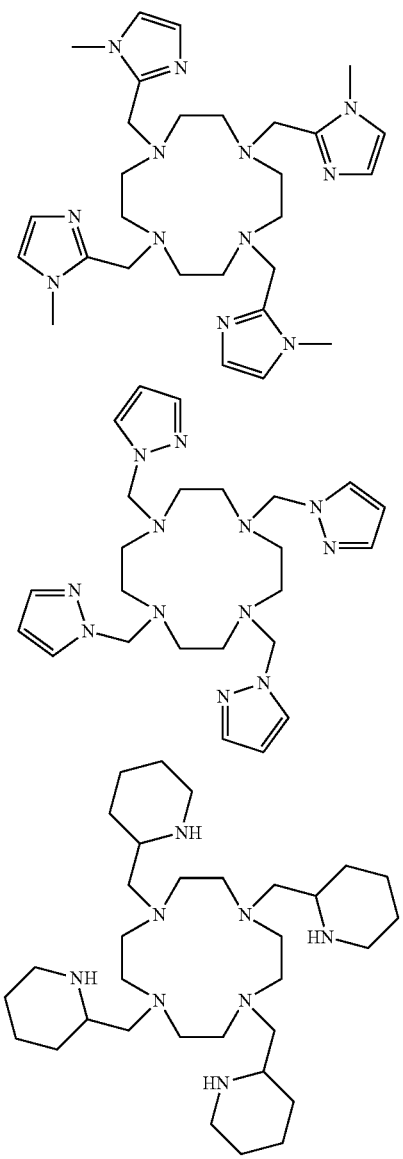

$^{225}$Ac/$^{213}$Bi Generator Elution Based on Selective Bi Complexation.

Because this class of ligands is selective for Bi over Ac, they can be applied as elution agents in a $^{225}$Ac/$^{213}$Bi generator, where the Bi-213 daughter will be eluted as the positively charged, complexed species. The bifunctional ligands can also be used, and the eluted bismuth can directly be conjugated to biomolecules such as, but not limited to, peptides and antibodies, for therapeutic use. This strategy will reduce time and simplify radiolabeling.

$L^{py}$ exhibited the fastest complexation kinetics. $L^{pz}$ exhibited the slowest kinetics. There might be a correlation between rate of complexation and basicity of the ligand. Embodiment ligands shown below are expected to selectively complex bismuth from a mixture of radionuclides including actinium-225. These ligands include nitrogen heterocycles pyrazole, imidazole, and piperidine, respectively, as nitrogen donors that are all more basic than the pyridine donors of $L^{py}$.

Chelation of Pb-212.

Pb-212 ($t_{1/2}$=10.6 h) decays by β-emission to Bi-212 ($t_{1/2}$=1 h), which itself decays by α emission. Pb-212 can therefore be used as an in vivo generator for Bi-212 for TAT. The embodiment ligands, which are suitable for chelating Bi, may also be suitable for chelating $Pb^{2+}$.

The direct use of Ac-225 as a therapeutic radionuclide gives rise to toxic side effects arising from the migration of its daughter nuclides. A strategy to minimize these toxic side effects is the co-administration of ligands that selectively bind to the daughter nuclides, facilitating their clearance. Using commercially available thiol-containing ligands, this approach has previously been explored for Ac-225 with limited success. The selective Bi-binding properties of the embodiment ligands may be used for these applications.

Ligands $L^{py}$, $L^{pyd}$, $L^{pyr}$, and $L^{pz}$, may also be used for chelation of lanthanide ions, including radiolanthanide ions, in the +3 oxidation state. These lanthanide complexes may be useful for applications related to luminescent sensors, MRI contrast agents, and in radionuclide therapy and imaging. Details of the synthesis of some chelation complexes of these ligands with lanthanum are provided below.

Synthesis of [LaL$^{py}$(OTf)](OTf)$_2$, (i.e. 1)

A solution of L$^{py}$ (46 mg, 0.086 mmol) in 5 mL MeOH was added in a dropwise manner to a solution of La(OTf)$_3$ (50. mg, 0.085 mmol) in 5 mL MeOH. The combined reagents were then heated at 40° C. for 3 h. The colorless solution was concentrated to dryness under vacuum at 40° C. to give a white oily residue. The residue was dissolved in 1 mL CH$_3$CN. The slow vapor diffusion of Et$_2$O at room temperature into this solution afforded needle-like colorless crystals of the desired compound. The crystals were washed with 3×1 mL Et$_2$O and then dried in vacuo. Yield: 71 mg, 74%. IR (ATR, cm$^{-1}$): 2867 w, 1607 m, 1571 m, 1483 m, 1444 m, 1380 w, 1313 m, 1254 s, 1209 s, 1153 s, 1076 m, 1024 vs, 974 m, 907 w, 839 w, 812 m, 780 m, 758 s, 731 w. Analysis calcd. for 1, C$_{35}$H$_{40}$N$_8$F$_9$LaO$_9$S$_3$: C, 37.44; H, 3.59; N, 9.98. Found: C, 37.11; H, 3.87; N, 9.80.

Synthesis of [LaL$^{pyd}$(OTf)](OTf)$_2$.H$_2$O, (i.e. 2.H$_2$O)

A solution of L$^{pyd}$ (87 mg, 0.16 mmol) in 2 mL MeOH was added in a dropwise manner to a solution of La(OTf)$_3$ (94 mg, 0.16 mmol) in 3 mL MeOH. The combined reagents were then heated at 40° C. for 6 h. The pale yellow solution was concentrated to dryness under vacuum at 40° C. to give an oily orange residue. The residue was dissolved in 1.5 mL CH$_3$CN and filtered. The slow vapor diffusion of Et$_2$O at room temperature into this solution afforded pale yellow crystalline solid. This solid was dispersed in 1 mL CH$_3$CN, and then centrifuged. The solid, now white in color, was separated from the yellow supernatant, washed with 1.5 mL CH$_3$CN and 3×1 mL Et$_2$O, and dried in vacuo. Et$_2$O was allowed to vapor diffuse into the yellow supernatant, affording an additional crop of white crystalline product, which was washed with 3×1 mL Et$_2$O, and dried in vacuo. Yield: 40 mg (first crop)+26 mg (second crop), 36%. $^1$H NMR (400 MHz, D$_2$O, 5° C.): δ=8.98 (4H, t), 7.94 (8H, d+d), 4.57 (4H, br d), 4.02 (8H, br t), 3.52 (4H, br t), 2.80 (8H, br d). $^{13}$C{$^1$H} NMR (100 MHz, D$_2$O, 5° C.): δ=162.6, 152.7, 132.3, 131.1, 120.2 (q, $^1J_{CF}$=316 Hz), 59.0, 53.71 (br), 51.43 (br). IR (ATR, cm$^{-1}$): 3069 w, 2862 w, 1616 w, 1595 m, 1560 w, 1483 w, 1443 m, 1415 w, 1367 vw, 1251 vs, 1221 s, 1151 s, 1076 m, 1027 vs, 1007 s, 967 m, 904 w, 839 m, 815 m, 772 w, 756 w, 745 w. Anal. calcd. for 2.H$_2$O, C$_{31}$H$_{38}$N$_{12}$F$_9$LaO$_{10}$S$_3$: C, 32.52; H, 3.35; N, 14.68. Found: C, 32.47; H, 3.59; N, 14.59.

Synthesis of [LaL$^{pyr}$(OTf)](OTf)$_2$.MeOH, (i.e. 3.MeOH)

A solution of L$^{pyr}$ (100 mg, 0.18 mmol) in 3 mL MeOH was added in a dropwise manner to a solution of La(OTf)$_3$ (108 mg, 0.18 mmol) in 3 mL MeOH. The combined reagents were then heated at 40° C. for 6 h, and then allowed to cool to room temperature. The vapor diffusion of Et$_2$O at room temperature into the resulting yellow solution afforded white crystalline solid. The supernatant was decanted, and the solid was washed with 3×2 mL Et$_2$O and dried in vacuo. Yield: 130 mg, 62%. $^1$H NMR (400 MHz, D$_2$O, 5° C.): δ=9.03 (4H, d), 8.55 (4H, s), 7.86 (4H, d), 4.64 (4H, d), 4.04 (8H, m), 3.26 (4H, t), 2.81 (8H, m). $^{13}$C{$^1$H} NMR (100 MHz, D$_2$O, 5° C.): δ=166.7, 161.7, 158.3, 123.8, 120.2 (q, $^1J_{CF}$=315 Hz), 59.8, 53.6, 51.3. IR (ATR, cm$^{-1}$): 2873 w, 1593 s, 1554 m, 1483 w, 1460 w, 1400 m, 1312 m, 1253 vs, 1207 s, 1155 s, 1075 m, 1026 vs, 1002 m, 966 m., 906 s, 839 w, 812 w, 779 w, 740 w, 688 m. Anal. calcd. for 3.MeOH, C$_{32}$H$_{40}$N$_{12}$F$_9$LaO$_{10}$S$_3$: C, 33.17; H, 3.48; N, 14.50. Found: C, 33.73; H, 3.74; N, 14.81.

Synthesis of [LaL$^{pz}$(OTf)](OTf)$_2$.MeOH, (i.e. 4.MeOH)

L$^{pz}$ (50 mg, 0.092 mmol) was dissolved in 2 mL MeOH by heating the mixture to 50° C. The resulting solution of L$^{pz}$ was added to La(OTf)$_3$ (54 mg, 0.092 mmol) dissolved in 0.5 mL MeOH. Upon sitting at room temperature for 16 h without stirring, colorless plate-like crystals of the desired compound deposited. The supernatant was carefully removed with a Pasteur pipette, and the crystals were washed sequentially with 3×2 mL hot (40° C.) MeOH and 3×2 mL Et$_2$O. The remaining solid was dried in vacuo at room temperature. Yield: 27 mg (25%). $^1$H NMR (400 MHz, D$_2$O, 5° C.): δ=8.67 (4H, s), 8.64 (4H, d), 8.17 (4H, unresolved d), 4.44 (4H, d), 3.92 (8H, d), 3.22 (4H, br t), 2.66 (8H, br t). $^{13}$C{$^1$H} NMR (100 MHz, D$_2$O, 5° C.): δ=152.8, 147.0, 145.7, 144.5, 120.2 (q, $^1J_{CF}$=315 Hz), 57.8, 53.1, 51.0. IR (ATR, cm$^{-1}$): 2862 w, 1481 w, 1458 w, 1420 w, 1374 w, 1255 vs, 1222 m, 1150 s, 1080 m, 1027 vs, 1007 m, 968 w, 902 w, 855 w, 840 w, 803 w, 774 w, 752 w, 676 w. Anal. calcd. for 4.MeOH, C$_{32}$H$_{40}$N$_{12}$F$_9$LaO$_{10}$S$_3$: C, 33.17; H, 3.48; N, 14.50. Found: C, 32.70; H, 3.95; N, 14.59.

Single crystals of L$^{pyd}$ and L$^{pyr}$ were obtained by the slow evaporation of methanolic solutions. Crystals of L$^{pz}$ were grown by the vapor diffusion of Et$_2$O into a DMF solution. Vapor diffusion of Et$_2$O into CH$_3$CN solutions of 1 and 2 afforded X-ray quality crystals. Weakly diffracting and highly twinned crystals of 3 and 4 were obtained by the vapor diffusion of Et$_2$O into a methanolic solution and directly from the methanol reaction solvent, respectively.

Single crystals were mounted on nylon loop in n-paratone oil and cooled with a Bruker Kryoflex nitrogen cold stream. A Bruker D8 diffractometer with a graphite monochromatized Mo Kα X-ray source (λ=0.71073 Å), controlled by the APEX2 software package, was used for data collection. Data were integrated with SAINT, and subsequently corrected for absorption with SADABS. The SHELXTL software package was employed for structure solution and refinement against F$^2$. Heavy atoms were located on the difference Fourier map and refined anisotropically. Hydrogen atoms were placed at calculated positions and given isotropic thermal parameters equal to either 1.5 (terminal CH$_3$ groups) or 1.2 times that of thermal parameter of the atom to which they were attached. For the ligands L$^{pyd}$, L$^{pyr}$, and L$^{pz}$, the locations of the nitrogen atoms on the heterocycles were assigned by careful analysis of the difference Fourier map prior to hydrogen-atom placement. No electron density corresponding to hydrogen atoms was located at the atoms assigned as nitrogen atoms, whereas the other atoms on the heterocycle clearly displayed residual density arising from hydrogen atoms. L$^{pyr}$ crystallized in the non-centrosymmetric space group, Pna2$_1$. Because of the lack of heavy atoms in the structure of L$^{pyr}$, the absolute structure was not refined. In the structure of 1, the oxygen atom of a disordered molecule of diethyl ether was located on a crystallographic 2-fold axis. The geometries of the disordered components were refined with similarity restraints (SADI, default values), and sum of the occupancy of the components was constrained to unity. The thermal displacement parameters of this disordered molecule were also restrained to have similar size and shape (SIMU and DELU, default values). For 2, after identifying and assigning all species in the asymmetric unit, several peaks of residual electron density remained. The electron density was refined as four water molecules, disordered spatially within this void. The sum of the occupancy of the four oxygen atoms was constrained to unity. The thermal ellipsoids of the oxygen atoms were restrained to be spherical (ISOR, default values) and constrained be identical (EADP). Because of the low occupancy of each oxygen atom, hydrogen atoms were neither located on the difference Fourier map, nor included in the final model. Table 1 below summarizes X-ray crystallographic data collection and refinement parameters for Lpyd, Lpyr, Lpz, 1.0.5Et$_2$O, and 2.H$_2$O.

TABLE 1

|  | L$^{pyd}$ | L$^{pyr}$ | L$^{pz}$ | 1•0.5Et$_2$O | 2•H$_2$O |
|---|---|---|---|---|---|
| formula | C$_{28}$H$_{36}$N$_{12}$ | C$_{28}$H$_{36}$N$_{12}$ | C$_{28}$H$_{36}$N$_{12}$ | C$_{41}$H$_{51}$F$_9$LaN$_{10}$O$_{9.50}$S$_3$ | C$_{33}$H$_{39}$F$_9$LaN$_{13}$O$_{10}$S$_3$ |
| fw | 540.69 | 540.69 | 540.69 | 1242.01 | 1183.86 |
| space group | P$\bar{1}$ | Pna2$_1$ | P2$_1$/n | Pbcn | P2$_1$/n |
| a, Å | 8.8576 (5) | 16.343 (5) | 11.6230 (15) | 34.084 (5) | 12.945 (4) |
| b, Å | 9.6141 (6) | 12.689 (4) | 10.0308 (13) | 13.3725 (19) | 27.498 (8) |
| c, Å | 9.6564 (6) | 13.491 (4) | 11.6987 (15) | 21.967 (3) | 13.200 (4) |
| α, ° | 106.408 (4) |  |  |  |  |
| β, ° | 91.713 (4) |  | 99.7720 (10) |  | 91.262 (4) |
| γ, ° | 115.409 (4) |  |  |  |  |
| V, Å$^3$ | 701.61 (7) | 2797.8 (14) | 1344.1 (3) | 10012 (2) | 4698 (2) |
| Z | 1 | 4 | 2 | 8 | 4 |
| ρ$_{calcd}$, g · cm$^3$ | 1.280 | 1.284 | 1.336 | 1.648 | 1.674 |
| T, K | 140 (2) | 140 (2) | 140 (2) | 140 (2) | 140 (2) |
| μ(Mo Kα), mm$^{-1}$ | 0.083 | 0.083 | 0.086 | 1.076 | 1.145 |
| θ range, ° | 2.23 to 28.87 | 2.03 to 25.12 | 2.28 to 27.48 | 1.85 to 27.24 | 1.48 to 25.13 |
| total data | 16845 | 25569 | 14616 | 106007 | 53829 |
| unique data | 3637 | 4970 | 3055 | 11193 | 8352 |
| parameters | 181 | 361 | 181 | 675 | 636 |
| restraints | 0 | 1 | 0 | 38 | 25 |
| completeness (%) | 99.0 | 99.9 | 99.5 | 99.8 | 99.2 |
| R$_1$$^a$ (%) | 5.09 | 3.24 | 3.69 | 3.17 | 6.41 |
| wR$_2$$^b$ (%) | 9.40 | 6.93 | 9.28 | 7.34 | 15.83 |
| GoF$^c$ | 1.011 | 1.033 | 1.039 | 1.051 | 1.060 |
| max, min peaks, e · Å$^3$ | 0.276, −0.237 | 0.160, −0.168 | 0.301, −0.244 | 1.436, −0.843 | 1.709, −1.096 |

$^a$R$_1$ = Σ||F$_o$| − |F$_c$||/Σ|F$_o$| for I > 2σ.
$^b$wR$_2$ = {Σ[w(F$_o$$^2$ − F$_c$$^2$)$^2$]/Σ[w(F$_o$$^2$)$^2$]}$^{1/2}$ for I > 2σ.
$^c$GoF = {Σ[w(F$_o$$^2$ − F$_o$$^2$)$^2$]/(n − p)}$^{1/2}$, where n is the number of data and p is the number of refined parameters.

Synthesis of Lanthanide(III) Complexes and Characterization

Coordination compounds of L$^{py}$, L$^{pyd}$, L$^{pyr}$, and L$^{pz}$ with lanthanum ions ("La$^{+3}$") were synthesized by reacting lanthanum(III) triflate (La(OTf)$_3$) with each ligand in methanol at 40° C. The resulting compounds 1, 2, 3, and 4 have the general formula, [La(L)(OTf)](OTf)$_2$, where L=L$^{py}$, L$^{pyd}$, L$^{pyr}$, and L$^{pz}$, respectively. Compound 4 crystallized out of solution directly. Compounds 1, 2, and 3 were soluble in methanol. Compounds 1, 2, 3, and 4 (also referred to as "complexes") were characterized by IR spectroscopy, elemental analyses, and X-ray crystallography. Their IR spectra included similar vibrational features. Elemental analyses were consistent with their proposed compositions.

Figure 5:
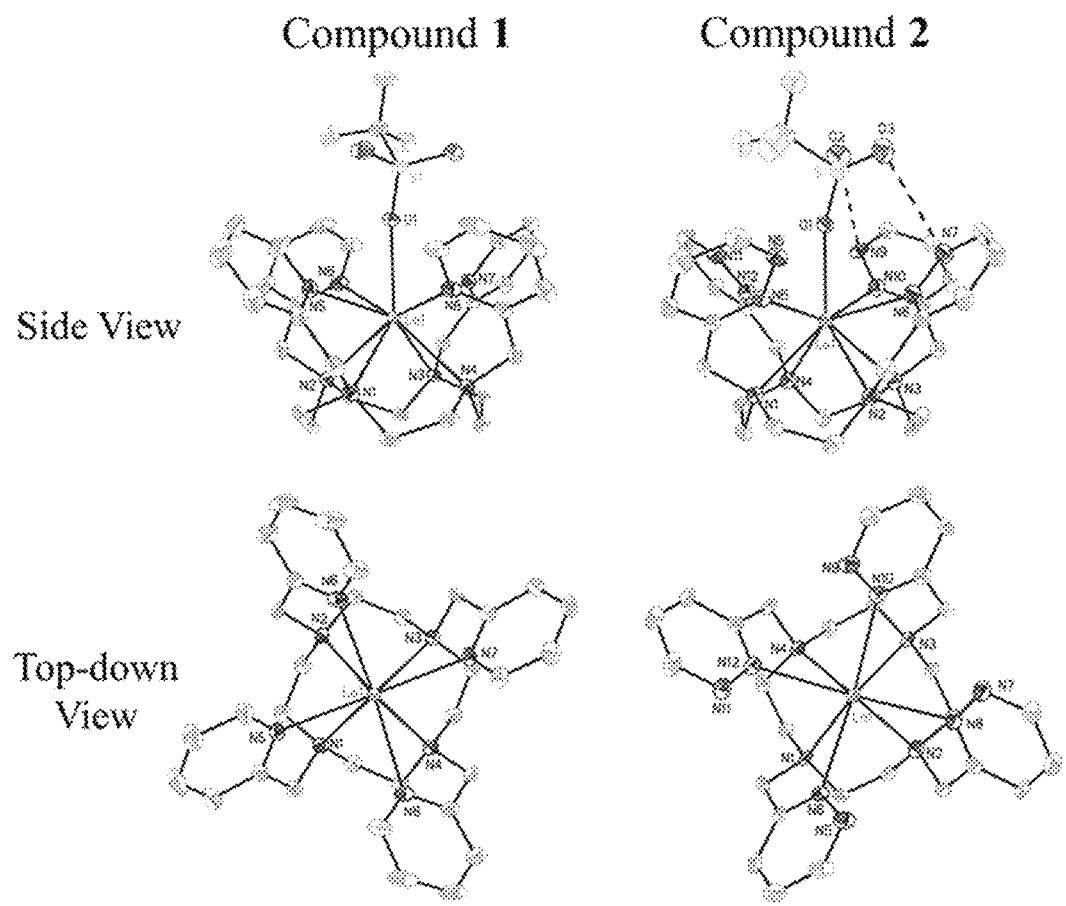
FIG. 5 shows X-ray crystal structures of chelation complexes 1 (left) and 2 (right) from a side view (top) and top-down view (bottom). The hydrogen atoms were omitted for clarity. In the top-down perspective, the coordinated triflate ligand has been removed. Ellipsoids are drawn at 50% probability levels.

X-ray crystal structures of 1 and 2 are shown in FIG. 5. For each structure, the coordination sphere of the La$^{3+}$ ion includes eight nitrogen-donor atoms arranged in a twisted square-antiprismatic (TSAP) geometry and a triflate counterion that occupies the axial coordination site. Two additional triflate ions are present in the outer-sphere and balance the charge of the complex. Compound 1 is isomorphous with the corresponding known Nd$^{3-}$ and Eu$^{3+}$ complexes of L$^{py}$. The sum of the interatomic distances for the inner coordination sphere of 1 is 24.187(6) Å, whereas for the Nd$^{3+}$ and Eu$^{3+}$ complexes these values are 23.78(2) and 23.51(4) Å, respectively. This decrease in interatomic distances is consistent with effects due to the well-known lanthanide contraction.

Figure 6:
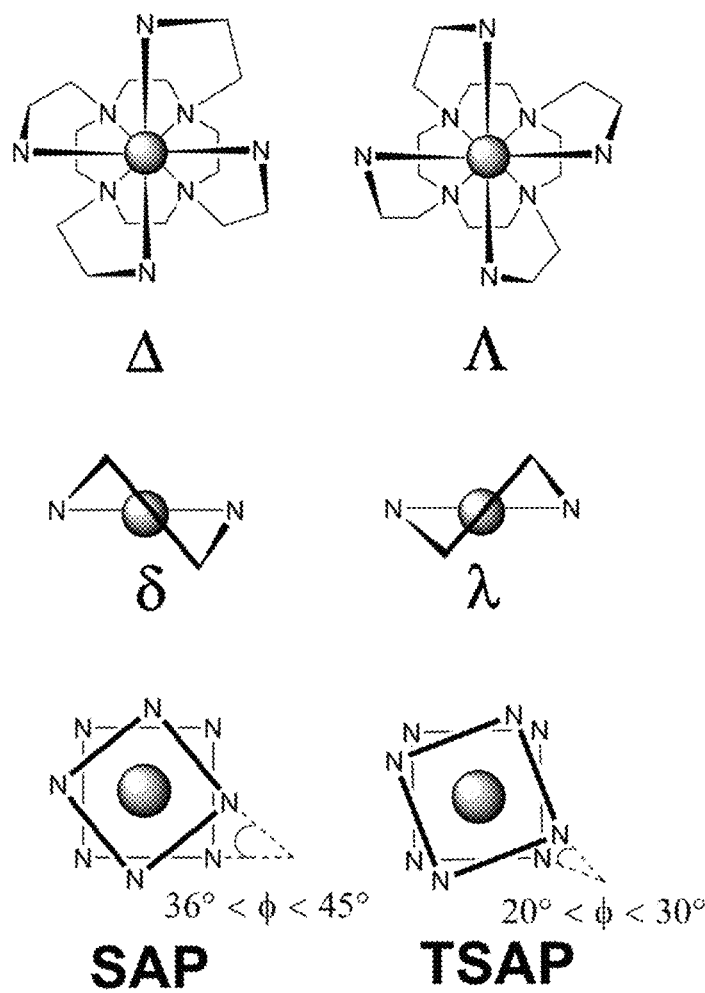
FIG. 6 schematically depicts chirality and diastereomers of some embodiment coordination complexes.

By analogy to the lanthanide complexes of DOTA, two stable diastereomers for each ligand are possible (see FIG. 6). The chirality of the helical twist of the pendant carboxylate groups of DOTA and pendant N-heterocycles of the embodiment ligands is denoted by Δ or Λ (FIG. 6). The chirality of each of the four 5-membered chelate rings formed by the cyclen macrocycle is indicated with lowercase δ or λ (FIG. 6). Based on these two sources of chirality, two stable diastereomers exist, namely Λ(λλλλ) and Λ(δδδδ), with the corresponding enantiomers Δ(δδδδ) and Δ(λλλλ). Complexes of the Λ(λλλλ)/Δ(δδδδ) stereochemistry have a TSAP geometries; the twist angle (ϕ) between the plane of the four nitrogen atoms on the cyclen macrocycle and the plane of the four pendant donor atoms ranges from 20 to 30°. Complexes of Λ(δδδδ)/Δ(λλλλ) stereochemistry have a square-antiprismatic (SAP) geometry; the twist angle (ϕ) ranges from 36 to 45° (FIG. 6). For DOTA and related ligands, the TSAP isomer is energetically preferred for the earlier lanthanide ions. The SAP geometry is stabilized in the mid to late lanthanide ions, which have smaller ionic radii. The two diastereomers give rise to complexes that can have substantially different water-exchange rates. Therefore, knowledge of the relative populations of these diastereomers and their ability to interconvert may be used for designing lanthanide complexes for luminescence and MRI sensing.

Compounds 1 and 2 have TSAP geometries. Both enantiomers, Λ(λλλλ) and Δ(δδδδ), are present in the centrosymmetric crystal lattices of 1 and 2. In FIG. 6, the Λ(λλλλ) enantiomer of 1 depicted and the Δ(δδδδ) enantiomer of 2 are shown. Heavier lanthanide ions have smaller ionic radii due to the lanthanide contraction and form complexes of L$^{py}$ with SAP geometries.

Specific structural data for 1, 2, and related La$^{3+}$ complexes are given in Table 2 below.

TABLE 2

| complex | $\phi(°)^b$ | average La—N$_{cyclen}$ distance (Å) | average La—N/O$_{pendant}$ distance (Å) | axial-La distance (Å) | La—N$_4$(cyclen)-centroid distance (Å) | La—N$_4$(pendant) centroid distance (Å) |
|---|---|---|---|---|---|---|
| 1 | 23.9 | 2.713(4) | 2.699(4) | 2.5374(18) | 1.71 | 0.83 |
| 2 | 24.9 | 2.74(1) | 2.69(1) | 2.498(5) | 1.76 | 0.71 |
| [LaL$^{2quin}$(OCH$_3$)]$^{2+c}$ | 24.4 | 2.780(3) | 2.889(3) | 2.149(4) | 1.82 | 0.71 |
| Na[La(HDOTA)La(DOTA)] | 23.0 | 2.794(3) | 2.493(3) | 2.568(5) | 1.835 | 0.70 |
|  | 24.5 | 2.769(3) | 2.492(3) | 2.537(5) | 1.810 | 0.73 |
| [La(DOTAM')]$^{3+d}$ | 26.7 | 2.718(3) | 2.423(3) | N/A | 1.63 | 1.23 |
| [La(DOTAM-glycol)Cl]$^{2+e}$ | 37.7 | 2.788(4) | 2.501(3) | 2.811(3) | 1.81 | 0.54 |
| [La(THED)(OH$_2$)]$^{3+f}$ | 13.3 | 2.69(1) | 2.38(2) | 2.57(3) | 1.68 | 0.95 |

$^b$Twist angle - see FIG. 6.
$^c$L$^{2quin}$ = 1,4,7,10-tetrakis(2'-quinolylmethyl)-1,4,7,10-tetraazacyclododecane.
$^d$DOTAM' = 1,4,7,10-tetrakis(2-carbamoylethyl)-1,4,7,10-tetraazacyclododecane.
$^e$DOTAM-glycol = 2,2',2'',2'''-(1,4,7,10-tetraazacyclododecane-1,4,7,10-tetrayl)-tetrakis[N-[2-(2-hydroxyethoxy)ethyl]acetamide].
$^f$THED = 1,4,7,10-tetrakis(2-hydroxyethyl)-1,4,7,10-tetraazacyclododecane.

Table 2, second column lists the twist angles for each of the complexes. The twist angles for 1 and 2 are nearly identical (24° and 25°, respectively). The twist angles for [La(DOTAM-glycol)Cl]$^{2+}$ and [La(THED)(OH2)]$^{3+}$ are much larger and smaller, respectively. The larger twist angle of [La(DOTAM-glycol)Cl]$^{2+}$ likely arises as a consequence of its existence in the solid-state as the SAP isomer. La—N distances for 1 and 2 range from 2.66 to 2.75 Å. Average La—N$_{cyclen}$ distances are slightly larger than the average La—N$_{pendant}$ distances for both complexes. The related La$^{3+}$ complex, [LaL$^{2qinn}$(OCH$_3$)]$^{2+}$ where the pendant N-heterocycles of 1 and 2 are replaced by 2-quinoline, is structurally similar. The La—N$_{pendant}$ distances (average 2.889(3) Å) of this complex are substantially greater than those of 1 and 2, possibly due to greater steric hindrance of the quinolone arms or to strong electron donating properties of the anionic methoxide axial ligand. The La—OTf distance of 2 is marginally smaller than that of 1. An additional intramolecular interaction was observed in the structure of 2; the two non-coordinating oxygen atoms of the triflate ligand are in close contact with the non-coordinating nitrogen atoms of the pendant pyridazine ligands. This interaction is expected to be repulsive because both nitrogen and oxygen atoms carry partial negative charge.

X-ray crystal structures of complexes 3 and 4 were also obtained. Even with poorer resolution and weaker intensities of reflections and the presence of multiple twin domains, the X-ray crystal structures unambiguously identified the atomic connectivity of the complexes. The X-ray crystal structures show 3 and 4 with TSAP geometries in which lanthanum is coordinated to the octadenate ligands and to an axial triflate ligand.

$^1$H and $^{13}$C NMR spectra of 1-4 in D$_2$O in the temperature range of 5-95° C. reveal the presence of a single diastereomer that is believed to be the TSAP isomer. The peaks in the aromatic regions of the $^1$H and $^{13}$C NMR spectra suggest that the complexes have C$_4$-symmetry in solution. The peaks in the aliphatic regions for 1-4 have different widths; this suggests different degrees of conformational rigidity. The non-equivalency of peaks in the $^{13}$C NMR spectra due to the cyclen backbone further indicates that complexes 1-4 are locked into a single conformation.

Variable-temperature NMR spectroscopy was used to further probe the conformational dynamics of complexes 1-4. Raising the temperature from 5 to 95° C., resulted in broadening and coalescence of the muliplets of 1-4 in the aliphatic region of the $^1$H NMR. In the $^{13}$C NMR spectra, the two resonances near 53 and 60 ppm that correspond to the carbon atoms of the cyclen macrocycle broadened and coalesced into a single peak. Line-shape analysis of the coalescence provides first-order rate constants at different temperatures for the interconversion of these two carbon atoms. The resulting data can be evaluated with an Eyring analysis using equation (1) below, wherein k is the rate constant, T is the temperature in Kelvin, R is the gas constant, k$_B$ is the Boltzmann constant, h is Planck's constant, to yield a straight line from which the enthalpy and entropy of activation ($\Delta H^{\ddagger}$ and $\Delta S^{\ddagger}$) can be calculated.

$$\ln\frac{k}{T} = \frac{-\Delta H^{\ddagger}}{RT} + \ln\frac{k_B}{h} + \frac{\Delta S^{\ddagger}}{R} \qquad (1)$$

From the $\Delta H^{\ddagger}$ and $\Delta S^{\ddagger}$ values, the free energy of activation ($\Delta G^{\ddagger}$) and the first order rate in constant at 298 K were calculated according to equations 2 and 3 below.

$$\Delta G^{\ddagger} = \Delta H^{\ddagger} - T\Delta S^{\ddagger} \qquad (2)$$

$$k = \frac{k_B T}{h} e^{\frac{-\Delta G^{\ddagger}}{RT}} \qquad (3)$$

These activation parameters correspond to the interconversion of the carbon atoms on the cyclen macrocycle.

At all temperatures studied, only the major TSAP isomer was detected. The activation parameters presented here correspond to the lowest energy pathway that renders the two carbon atoms chemically equivalent.

The $\Delta G^{\ddagger}$ values for complexes 1-4 vary from 60 to 66 kJ/mol. The changes in $\Delta H^{\ddagger}$ and $\Delta S^{\ddagger}$ vary more widely. Decreases in $\Delta H^{\ddagger}$ are compensated by more negative values of $\Delta S^{\ddagger}$, leading to the modest differences of $\Delta G^{\ddagger}$ across the series. The $\Delta G^{\ddagger}$ value for the La$^{3+}$ complex of DOTA is 60.7 kJ/mol.

A systematic decrease in both $\Delta H^{\ddagger}$ and $\Delta S^{\ddagger}$ occurs in the order of 1>2>3>4. This sequence also follows that of the relative pK$_a$ values of the pendant heterocycles; pyridine is the most basic (pK$_a$ 5.23), followed by pyridazine (pK$_a$ 2.33), pyrimidine (pK$_a$ 1.30), and pyrazine (pK$_a$ 0.65). The large negative entropy of activation of 4, $-93\pm11$ J·K$^{-1}$·mol$^{-1}$, is noteworthy. The La$^{3+}$ complex of the pendant alcohol donor ligand THED (1,4,7,10-tetrakis(2-hydroxyethyl)-1,4,7,10-tetraazacyclododecane) exhibited a $\Delta S^{\ddagger}$ of $-58$ J·K$^{-1}$·mol$^{-1}$, and the Lu$^{3+}$ complex of a derivative of DOTA, where the anionic carboxylate arms are replaced by neutral pendant N-[2-(2-hydroxyethoxy)-ethyl]acetamide donors, possessed similar activation parameters as well, with $\Delta H^\ddagger=33\pm3$ kJ/mol and $\Delta S^\ddagger=-109\pm7$ J·K$^{-1}$·mol$^{-1}$. The observance of such large and negative $\Delta S^\ddagger$ for what should be an intramolecular process were not fully explained or understood for these complexes. These $\Delta S^\ddagger$ values may signify an increase in symmetry in the transition state. However, the transition state also encompasses the surrounding solvent molecules, whose reorganization may significantly contribute to the overall activation parameters observed. The presence of additional nitrogen atoms in the pendant heterocycles of 2-4 provide hydrogen-bond donors for interaction with water, which may alter the secondary solvation shell of the transition state more drastically than for that of 1.

The variable temperature NMR studies also showed that compound 1 was thermally stable in aqueous solution from 5° C. to 95° C. By contrast, 4 decomposed entirely at 95° C., yielding free ligand and a white precipitate presumed to be an insoluble lanthanum hydroxide. Initial signs of decomposition were observed by $^1$H NMR spectroscopy at 55° C. Compound 3 also decomposed; only about 33% of the complex remained after heating it to 95° C. Compound 2 was more stable; only 6-10% decomposition was observed at 95° C. The relative thermal stability correlates with the pK$_a$ of the pendant donor group. It is believed that the more basic heteocycles can stabilize the La$^{3+}$ complexes against the competing reaction with solvent water molecules.

The structures of the aqua analogues of 1-4, where the inner-sphere triflate ligand is replaced by a coordinated water molecule, were optimized in the gas-phase at the B3LYP/6-31G*/SDD(La) level of theory, as both the TSAP and SAP diastereomers. In agreement with the crystal structure analysis, the TSAP isomers are thermodynamically preferred by 15 to 25 kJ/mol. This large stabilization of the TSAP isomer explains the lack of observation of the SAP isomer in solution by NMR spectroscopy.

In summary, embodiment ligands are synthesized efficiently from commercially available reactants and are purified easily by recrystallization. Radiolabeling these ligands with bismuth ions is rapid at room temperature. These ligands selectively bind bismuth ions in the presence of competing quantities of radionuclides including actinium ions.

Although the present invention has been described with reference to specific details, it is not intended that such details should be regarded as limitations upon the scope of the invention, except as and to the extent that they are included in the accompanying claims.

What is claimed is:

1. A process, comprising:
    forming an aqueous mixture comprising a ligand, bismuth radionuclide ions, and actinium radionuclide ions to form a cationic complex of the ligand and a bismuth radionuclide ion in the presence of the actinium radionuclide ions, the ligand having a structural formula

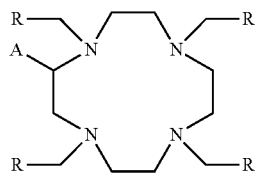

wherein A is selected from hydrogen and

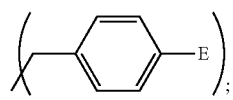

E is selected from —NO$_2$, —NH$_2$, —SCN, —N$_3$, -alkyne, maleimide, iodoacetamide, —NH(—C=S)NH—Z, triazole-Z, and thioether-Z; Z is a peptide, antibody, antibody fragment, peptide nucleic acid, nanoparticle, or other targeting moiety; and R is selected from

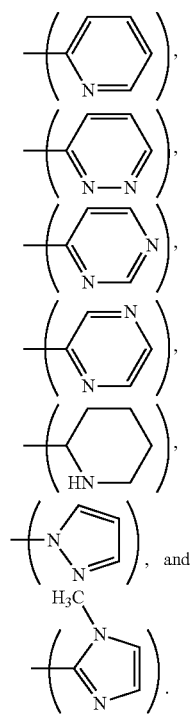

and
    separating the cationic complex of the bismuth radionuclide ion from the actinium radionuclide ions.

2. The process of claim 1, wherein the cationic complex has a structural formula

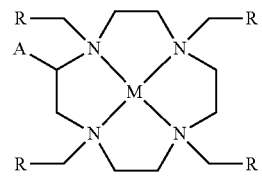

wherein:
    M is a metal ion;
    A is selected from hydrogen and

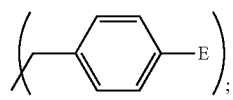

E is selected from —NO$_2$, —NH$_2$, —SCN, —N$_3$, -alkyne, maleimide, iodoacetamide, —NH(—C=S)NH—Z, triazole-Z, and thioether-Z;

Z is a peptide, antibody, antibody fragment, peptide nucleic acid, nanoparticle, or other targeting moiety; and R is selected from

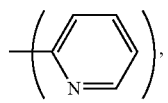

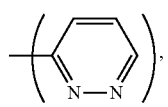

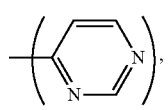

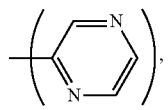

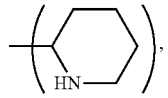

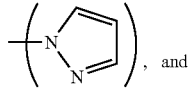

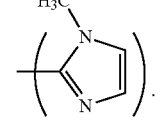

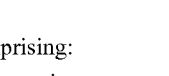

3. A method, comprising:

forming an aqueous mixture comprising bismuth radionuclide ions, actinium radionuclide ions and a ligand having a formula

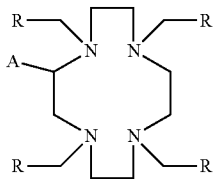

wherein A is selected from hydrogen and

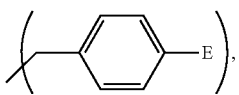

E is selected from —NO$_2$, —NH$_2$, —SCN, —N$_3$, -alkyne, maleimide, iodoacetamide, —NH(—C=S)NH—Z, triazole-Z, and thioether-Z, Z is a peptide, antibody, antibody fragment, peptide nucleic acid, or nanoparticle, and R is selected from

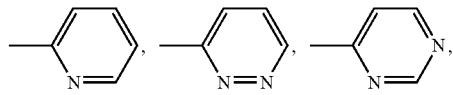

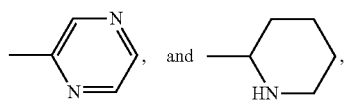

to form a cationic complex having a formula

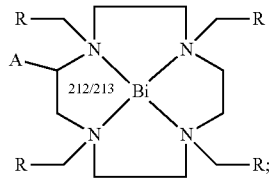

and separating the cationic complex from the actinium radionuclide ions.

4. The method according to claim 3 wherein:

the ligand has a formula

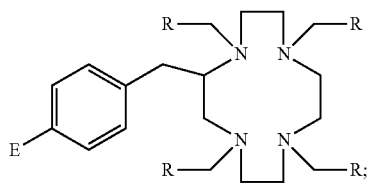

and the cationic complex has a formula

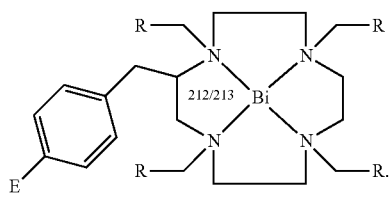

5. The method according to claim 3, wherein the ligand is selected from

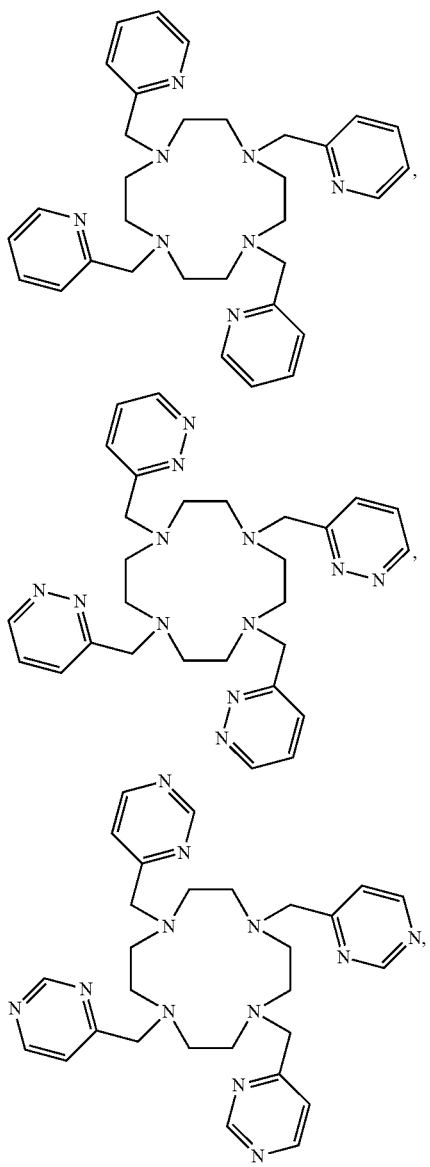

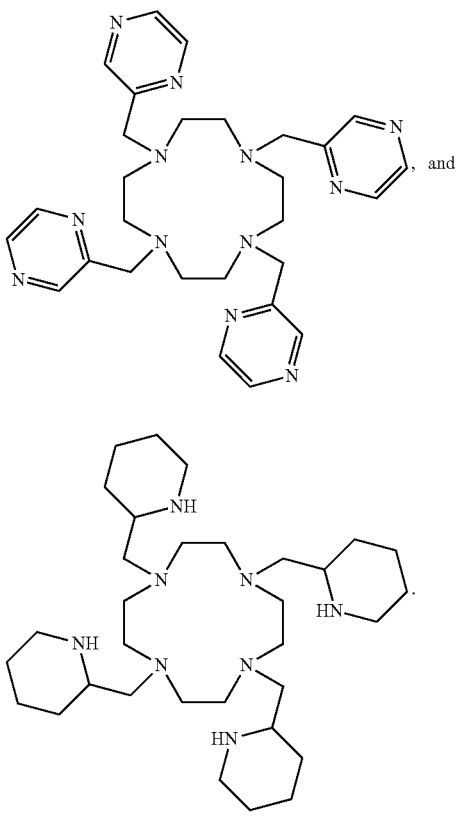 [SMILES: c1cnc(CN2CCN(Cc3cnccn3)CCN(Cc3cnccn3)CCN(Cc3cnccn3)CC2)cn1 ; C1CCC(CN2CCN(CC3CCCCN3)CCN(CC3CCCCN3)CCN(CC3CCCCN3)CC2)NC1]

6. The method according to claim 3, wherein A is

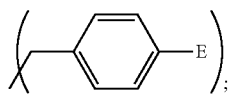

7. The method according to claim 3, wherein the aqueous mixture further comprises francium radionuclide ions, and separating the cationic complex from the actinium radionuclide ions further comprises separating the cationic complex from the francium radionuclide ions.

\* \* \* \* \*